United States Patent [19]

Coville et al.

[11] Patent Number: 4,818,493
[45] Date of Patent: Apr. 4, 1989

[54] APPARATUS FOR RECEIVING A TEST SPECIMEN AND REAGENT

[75] Inventors: William E. Coville, Levittown, Pa.; Hyman Grossman, Lambertville, N.J.; Michael Sokol, Melrose Park, Pa.

[73] Assignee: Bio/Data Corporation, Hatboro, Pa.

[21] Appl. No.: 43,113

[22] Filed: Apr. 27, 1987

Related U.S. Application Data

[62] Division of Ser. No. 793,376, Oct. 31, 1985, Pat. No. 4,695,430.

[51] Int. Cl.$^4$ .................. B01L 3/00; G01N 35/00
[52] U.S. Cl. ................................ 422/102; 422/61; 422/100
[58] Field of Search ..................... 422/63–67, 422/72, 73, 102, 104, 58, 61, 100

[56] References Cited

U.S. PATENT DOCUMENTS

| Re. 31,688 | 9/1984 | Popovich et al. | 604/6 |
|---|---|---|---|
| 3,437,452 | 4/1969 | Bell et al. | 23/309 |
| 3,504,376 | 3/1970 | Bednar et al. | 23/230 |
| 3,645,690 | 2/1972 | Rochte et al. | 23/230 R |
| 3,825,410 | 7/1974 | Bagshawe | 23/230 R |
| 3,883,306 | 5/1975 | Widen | 23/230 R |
| 3,932,131 | 1/1976 | Rolfo-Fontana | 23/230 R |
| 4,058,367 | 11/1977 | Gilford | 23/253 R |
| 4,105,547 | 8/1978 | Sandblom | 210/22 R |
| 4,113,436 | 9/1978 | Werder et al. | 422/65 |
| 4,191,182 | 3/1980 | Popovich et al. | 128/214 R |
| 4,212,742 | 7/1980 | Solomon et al. | 210/247 |
| 4,257,862 | 3/1981 | Schnipelsky et al. | 204/195 R |
| 4,269,803 | 5/1981 | Jessop | 422/63 |
| 4,302,420 | 11/1981 | Jakubowicz et al. | 422/63 |
| 4,338,279 | 7/1982 | Orimo et al. | 422/64 |
| 4,341,736 | 7/1982 | Drbal et al. | 422/100 |
| 4,343,705 | 8/1982 | Legg | 210/637 |
| 4,431,307 | 2/1984 | Suovaniemi | 356/246 |
| 4,497,774 | 2/1985 | Scordato | 422/73 |
| 4,515,753 | 5/1985 | Smith et al. | 422/102 |
| 4,528,159 | 7/1985 | Liston | 422/65 |
| 4,549,952 | 10/1985 | Columbus | 422/100 |
| 4,663,126 | 5/1987 | Gould et al. | 422/58 |

Primary Examiner—Michael S. Marcus
Attorney, Agent, or Firm—Seidel, Gonda, Lavorgna & Monaco

[57] ABSTRACT

An apparatus for automatically performing analytical testing of individual distant samples of biological fluids wherein a test sample is reacted with test reagents and tested for a change in optical characteristics. A memory stores a plurality of different test protocols. An operator-actuated keyboard is used to select one of the test protocols from the memory. Individual distinct samples of biological fluid to be tested are received in a sample cell. The cell is heated to a preselected temperature. The apparatus transports an individual sample cell to a first location adapted to filter unwanted nonfluid material from the fluid to be tested and to remove excess fluid to be tested from the sample cell to cause a precise accurate volume of fluid to remain in the sample cell for testing. After filtering and removal of excess fluid, the apparatus transports the individual sample cell from the first location to a second location for introducing a first reagent into the sample, and then transports the sample cell from the second location to a test location where a second reagent is introduced into the sample. An optical detector at the test location optically scans the sample in a vertical direction to detect a change in an optical characteristic of the sample. The apparatus provides an alphanumeric indication that a change in the optical characteristic in the sample has been detected. The invention includes a uniquely configured sample cell for receiving the samples of fluid to be tested and unique apparatus for delivering precise volumes of a liquid reagent. A liquid reservoir is pressurized with gas to a preselected pressure and is automatically regulated to maintain the pressure at a constant value. A valve in conjunction with a nozzle and a conduit adapted to impart a constant flow rate to reagent being delivered is opened for precise, predetermined time intervals so that a precise predetermined volume of liquid flows through the valve in the predetermined time interval.

12 Claims, 19 Drawing Sheets

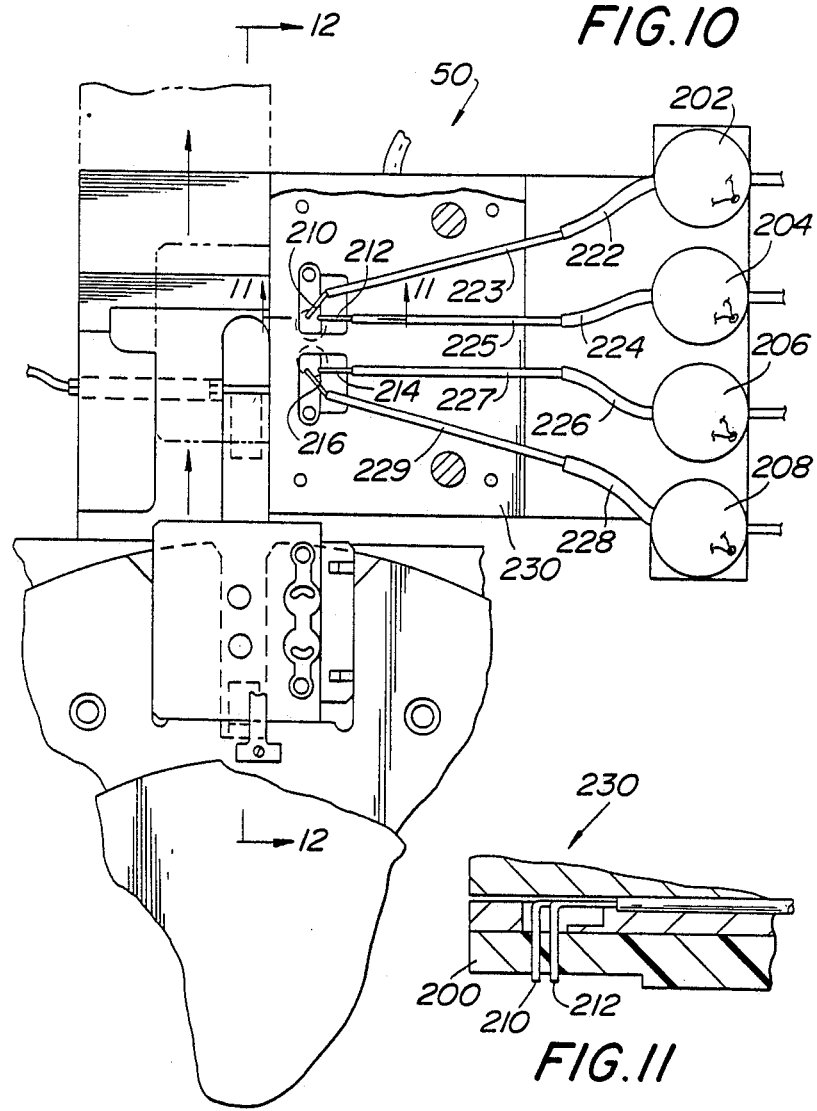

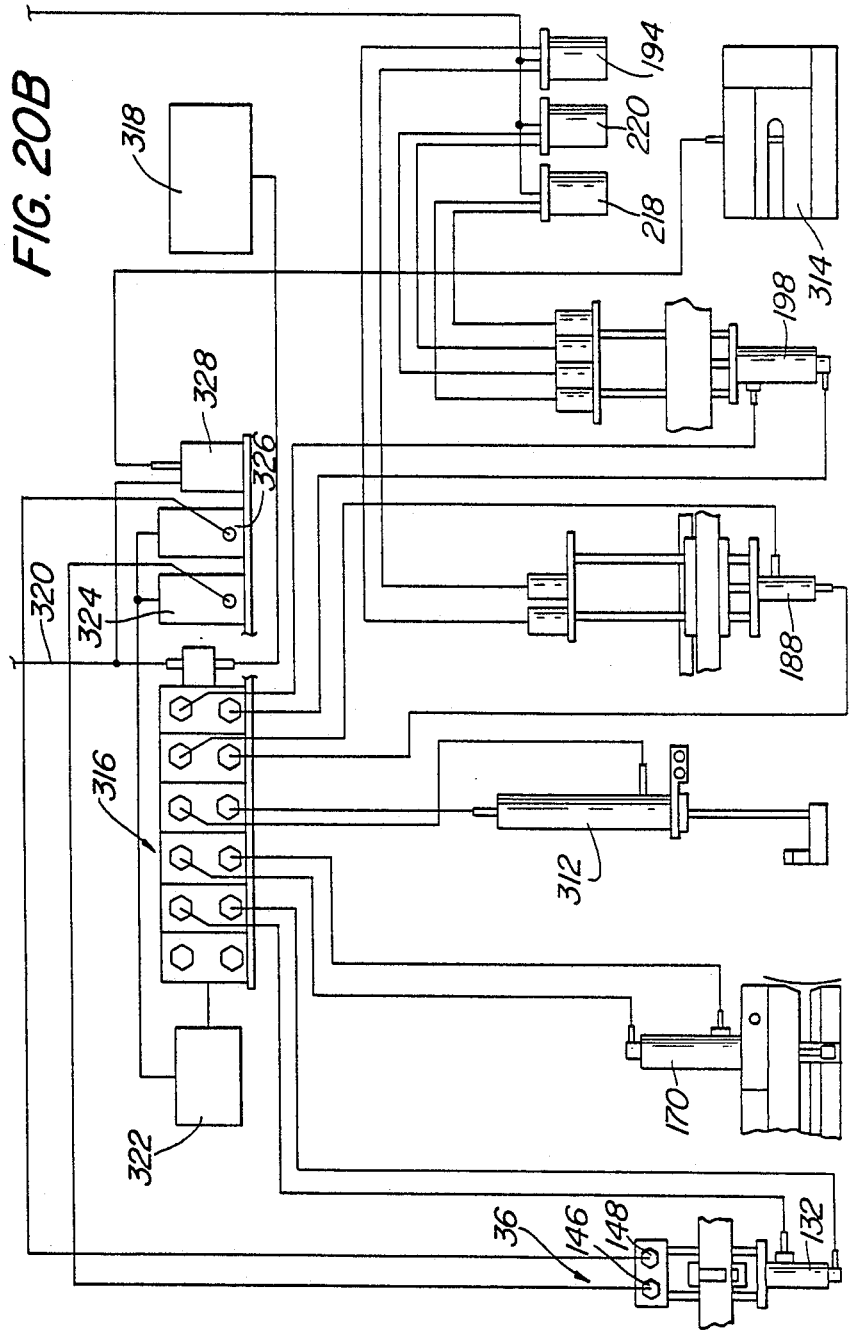

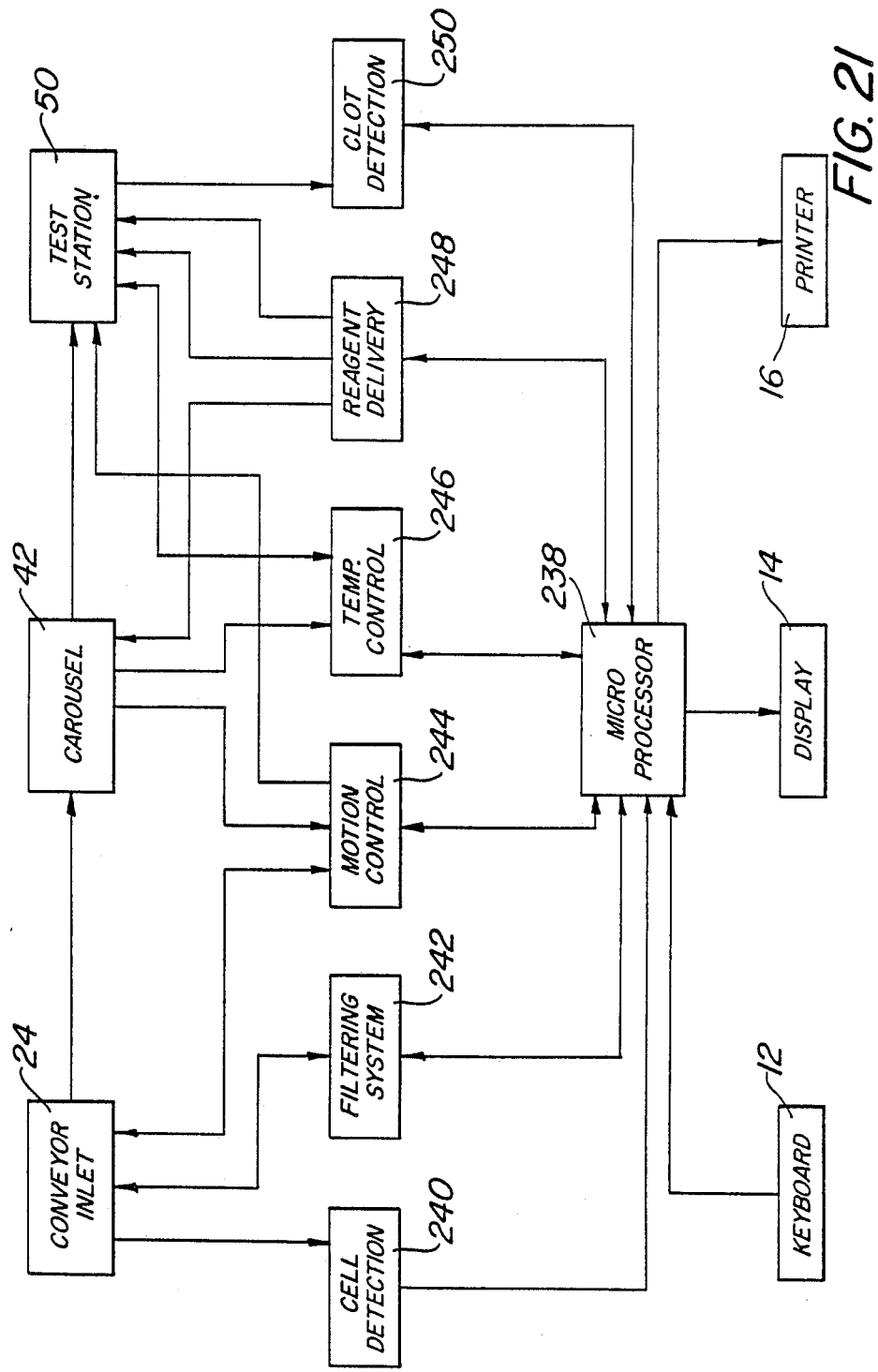

APPARATUS FOR RECEIVING A TEST SPECIMEN AND REAGENT

This is a divisional of co-pending application Ser. No. 793,376 filed on Oct. 31, 1985 now U.S. Pat. No. 4,695,430.

BACKGROUND OF THE INVENTION

The present invention is directed to automated analytical apparatus to detect the time of formation of fibrin clots in human or animal blood plasma by the prothrombin time (PT) test, the activated partial thromboplastin time (APTT) test, thrombin time test (TT) or other clotting factor tests and assays. The invention also has utility in other automated testing application in addition to blood coagulation, including but not limited to clinical chemistry, serology and the like.

Methods of detecting the formation of fibrin clots data back to the late 1870's. Such methods were manual. For example, in one test a white horse hair was drawn through a blood specimen. The endpoint of the clotting time was the point where shreds of fibrin could be visually detected on the hair. By 1910, an electrical apparatus called a "coaguloviscosimeter" was developed which directly measured the change in viscosity of a blood sample as it clotted. The apparatus provided a direct indication of voltage which could be plotted against clotting time.

In the early 1920's, rudimentary photoelectric techniques were developed to detect variations in light transmissivity of a blood sample during clotting. An apparatus termed a "nephelometer" was devised which consisted of a light source that furnished constant illumination to the sample. During coagulation of the sample, variations in the optical transmissivity of the sample were registered by a thermoplie connected to a sensitive galvanometer. By reading the movements of the galvanometer needle, transmissivity values could be plotted against elapsed time.

In the mid 1930's, investigations of the coagulation of blood plasma using more sophisticated photoelectric techniques were conducted. It was noted that an increase in density occurs as blood coagulates. The possibility of detecting this change by photoelectric techniques was investigated. This led to the development of an instrument which displayed increasing density of the sample as a gradual change in the voltage displayed by a galvanometer. In addition, a water bath was used to maintain the blood sample at 37° C.

Early photoelectric systems were limited to one specimen at a time, and there was no way to compensate for differences in plasma density and color variations from specimen to specimen. There was also no common reference point.

Today, five automated clotting time measurement techniques are in use: (1) electromechanical; (2) clot elasticity; (3) fibrin adhesion; (4) impedance; and (5) optical density. The principal electromechanical method in use today involves the use of a "fibrin switch" in which the physical formation of fibrin strands in a reaction mixture serves to complete an electrical circuit between two electrodes, thus stopping a timer. There are a number of limitations to "fibrin switch" systems. Clot formation cannot continually be observed. They are prone to cross-contamination and mechanical failure. An operator must clean the electrodes, exposing the operator to the risk of infection.

Clot elasticity analyzers consist of a pin, with an attached mirror, which rotates in a stainless steel cuvette which contains the plasma sample. Light is directed onto the mirror and is reflected from the mirror onto photosensitive film. As the clot develops, the elasticity of the sample changes, changing the mirror position and altering the pattern of light projected on the film. Either plasms or whole blood may be used, but whole blood testing is inferior to plasma testing because (1) extraneous factors in whole blood may affect test results, (2) test time is much longer, and (3) the test is much less specific.

In fibrin adhesion systems, a filament moves through the sample, and the clot adheres to the filament as the clot forms. The clot, which becomes attached to and moves with the filament, interrupts a light beam to initiate end point detection. Either plasma or whole blood may be used with this system.

In impedance detection systems, a special sensing probe is moved through a sample. As the clot forms, the probe movement is impeded. More energy is required to maintain the same degree of movement of the probe through the sample. The instrument displays a recording of the amount of energy required to keep the probe in motion. The amount of energy can be related to clotting time.

Optical density detection systems operate on the principle that an increase in density of the coagulating plasma will decrease the transmission of light through the sample. The test sample is placed in a transparent sample cuvette and reacted with a test reagent. Light is directed through the reacted sample. A typical test reagent usd in coagulation testing is a biological substance called thromboplastin, derived from brain tissue of rabbits. Such reagents are delicate and expensive. Advantages of optical systems include (1) no contact with sample, no cross-contamination, and no contacct activation by agitating the specimen; (2) continuous observation of clot formation, which yields increased reproducibility of test results; (3) a consistent end point; and (4) ease of automation, thereby minimizing human error.

Modern optical systems no longer depend on an absolute optical density change or a direct voltage reading from a photocell. Instead, modern systems operate on the first or second derivative of the photocell voltage. Thus, modern systems are independent of initial optical density or color of the sample.

Most optical detection systems in use today utilize lines of sight transverse to the sample cuvette. A few use lines of sight axial to the sample cuvette. In transverse line-of-sight detectors, a light source and photodetector are placed on diametrically opposite sides of the sample cuvette. Such transverse line-of-sight systems typically require large volumes of plasma and reagnet, because it is necessary, for accurate detection, to direct the light through approximately the central third of the sample. Since relatively large amounts of expensive test reagent are required, transverse line-of-sight detectors are expensive to operate.

In axial line-of-sight systems, a light source is located above the sample cuvette and the photodetector is located underneath the cuvette. With axial line-of-sight systems, the optics must compensate for the meniscus at the surface of the sample. Also, the volume of sample and reagent must be controlled to extremely close tolerances, since differences in liquid depth in the cuvette could alter the test results. Moreover, when the sample and the reagents are added to the cuvette, frothing of the sample may occur, resulting in a number of bubbles on and below the surface of the sample. The bubbles will lead to false readings and unreliable results.

No existing equipment integrates plasms separation from whole blood as part of the equipment in order to perform testing on plasma only.

It is an object of the present invention to provide an automated analytical apparatus to detect the time of formation of fibrin clots in human or animal blood plasma.

It is also an object of the invention to integrate plasma separation from whole blood as part of the automated analytical apparatus in order to perform testing on plasma only. By integrating plasma separation from whole blood as part of the apparatus, a separate prior and necessary centrifugation operation is eliminated. Accordingly, throughput of test samples can be increased. In addition, freshly-filtered plasma yields more accurate test results than plasma obtained by centrifugation.

It is also an object of the invention to provide an analytical apparatus which is "user friendly" and eliminates manual operations.

It is also an object of the invention to provide a disposable sample cell for receiving samples of fluid to be tested. Making the sample cell disposable reduces the possible risk of infection from blood samples.

SUMMARY OF THE INVENTION

The present invention is directed to apparatus for automatically performing analytical testing of individual distinct samples of biological fluids wherein one or more test reagents are introduced into the samples and the reacted samples are tested for a change in optical characteristics. The apparatus comprises memory means for storing a plurality of different test protocols and means for selecting one of said plurality of test protocols form the memory. A sample cell means for receiving the individual distinct sample of said plurality of test protocols from the memory. A sample cell means for receiving the individual distinct sample of biological fluid to be tested is provided. The apparatus has means for receiving an individual sample call and for sensing the presence of an individual sample cell. Means are provided for heating the individual sample cell to a preselected temperature. The apparatus has means for transporting an individual sample cell to a first location adapted to filter unwanted nonfluid material from the fluid to be tested and to remove excess fluid to be tested from the sample cell to cause a precise, accurate volume of fluid to be tested to remain in the sample cell. Means are provided for transporting the individual sample cell from the first location to a second location adapted to introduce a first reagent into the sample, and means are provided for transporting the individual sample cell from the second location to a test location. The test location has means for introducing a second reagent to the sample and means for optically scanning the sample in a vertical direction relative to the individual sample cell, and includes means for optically detecting a change in an optical characteristic of the sample. The apparatus has means for providing an indication that a change in the optical characteristic of the sample has been detected.

The invention also includes two different apparatuses for receiving a sample of fluid to be tested. One sample receiving apparatus has slide meand having at least one cavity in its top surface for receiving and holding a quantity of fluid to be tested and body means slideably engaged with the slide means. The slide means is slidable between a first position relative to the body means and a second position relative to the body means. The bottom surface of the body means faces the top surface of the slide means. The body means has at least one opening through it from its top surface to its bottom surface. The opening is in alignment with the cavity in the slide means when the slide means is in the first position whereby fluid to be tested is introduced into the cavity through the opening. The body means also has at least one downwardly opening chamber in it, the lower end of said chamber being in the same plane as the bottom surface of the body means and being substantially closed except for an opening through the bottom surface. The chamber has a downwardly projecting member extending from the upper end of the chamber into the chamber. The chamber is in alignment with the cavity in the slide means when the slide means is in the second position to form a test cell comprising the chamber and the cavity. The top surface of the slide means is in sliding contact with the bottom surface of the body means to from means for removing excess fluid to be tested from the cavity as the slide means moves relative to the body means from the first position to the second position. This causes a precise, accurate volume of fluid to remain in the cavity.

The other sample-receiving apparatus receives a sample of fluid containing non-fluid components and filters the non-fluid components from the fluid and comprises slide means having at least one cavity in its top surface for receiving and holding a quantity of filtered fluid to be tested and body means slideably engaged with the slide means. The slide means is slideable between a first position relative to the body means and a second position relative to the body means. The bottom surface of the body means faces the top surface of the slide means. The body means has a plurality of fluid flow channels in its top surface and at least one opening through the body means from the channels to the bottom surface. The opening communicates with the cavity in the slide means when the slide means is in the first position. A fluid reservoir means is located on the top surface of the body means above the fluid flow channels. The fluid reservoir means has two chambers, each chamber being substantially open at its top end and substantially closed at its bottom end except for an opening therethrough which communicates with the fluid flow channels. A filter means is located between the fluid flow channels and the openings in the bottom end of the fluid reservoir chambers for filtering the non-fluid components from the fluid. The body means also has at least one downwardly opening chamber therein separate from the fluid reservoir. The lower end of the chamber is in the same plane as the bottom surface of the body means and is substantially closed except for an opening therethrough. The chamber has a downwardly projecting member extending from the upper end of the chamber into the chamber. The chamber is in alignment with the cavity in the slide means when the slide means is in the second position to form a test cell comprising the chamber and the cavity. The top surface of the slide means is in sliding contact with the bottom surface of the body means to form means for removing excess fluid to be tested from the cavity as the slide means moves relative to the body means from the first position to the second position. This causes a precise accurate volume of fluid to remain in the cavity.

The invention further includes apparatus for delivering precise volumes of a liquid. The apparatus has at least one liquid reservoir for containing liquid to be delivered and means for pressurizing the liquid reservoir with a gas to a preselected pressure. Means for automatically regulating the preselected pressure to maintain the pressure at a constant value are provided. The apparatus has nozzle means for dispensing the liquid to be delivered into a receptacle and conduit means for conducting the liquid to be delivered from the reservoir to the nozzle means. The conduit means are adapted to impart a constant flow rate to liquid being conducted from the reservoir to the nozzle means. Valve means are located in the conduit means between the reservoir and the nozzle means. Means are provided for opening the valve means for precise, predetermined time intervals whereby a precise predetermined volume of liquid flows through the valve means in the predetermined time interval.

The invention also includes a method of delivering precise volumes of a liquid. The method comprises the steps of storing the liquid to be delivered in a reservoir, pressurizing the reservoir with a gas at a preselected pressure, automatically regulating the preselected pressure to maintain the pressure at a constant value and causing the liquid to be delivered to flow at a constant rate from the reservoir for precise, predetermined time intervals whereby precise, predetermined volumes of liquid flow from the reservoir in the predetermined time intervals.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 10 is a top plan view of the test station.

FIG. 11 is a partial sectional view of the sample test station showing test reagent dispensing nozzles taken along the ling 11—11 in FIG. 10.

FIG. 20A and 20B are simplified diagrams of the pneumatic system.

FIG. 21 is a block diagram of the overall control system for the apparatus of the present invention.

DESCRIPTION OF THE INVENTION

I. Overall Description

Figure 1:
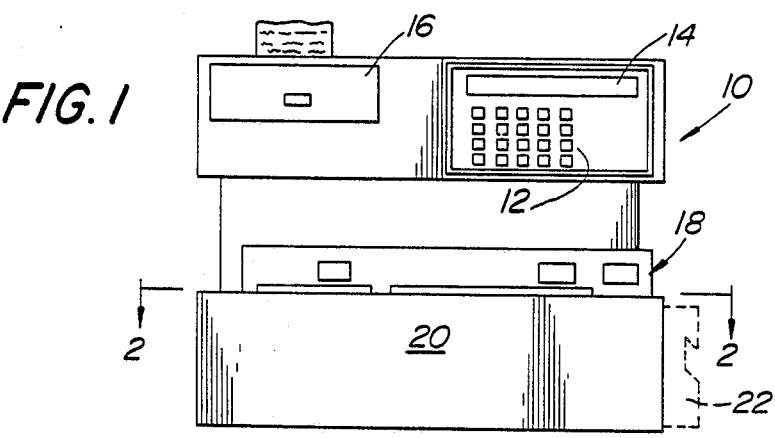
FIG. 1 generally illustrates the apparatus of the present invention.

Referring now to the drawings, wherein like numerals indicate like elements, there is shown in FIG. 1 an analytical apparatus 10 in accordance with the present invention. The apparatus has an operator keyboard 12 by which an operator may enter instructions and generally control operation of the apparatus 10. Associated with keyboard 12 is an alphanumeric display 14 by means of which prompts, status of the apparatus and other information may be visually displayed to an operator. A printing unit 16 is provided for making a printed record of test results for the tests performed on apparatus 10. Test results may also be displayed on alphanumeric display 14, or by any other visible display.

Below the operator keyboard 12 and printing unit 16 is located the sample cell handling and testing area 18. The sample cell handling and testing components of the invention will be described in greater detail below. A housing 20 contains themechanical and pneumatic parts necessary for operation of the invention. These parts will be described in greater detail below as required. At one side of housing 20 is located a removable waste bin 22, shown in phantom in FIG. 1. Waste bin 22 receives samples after testing for antiseptic disposal.

Figure 2:
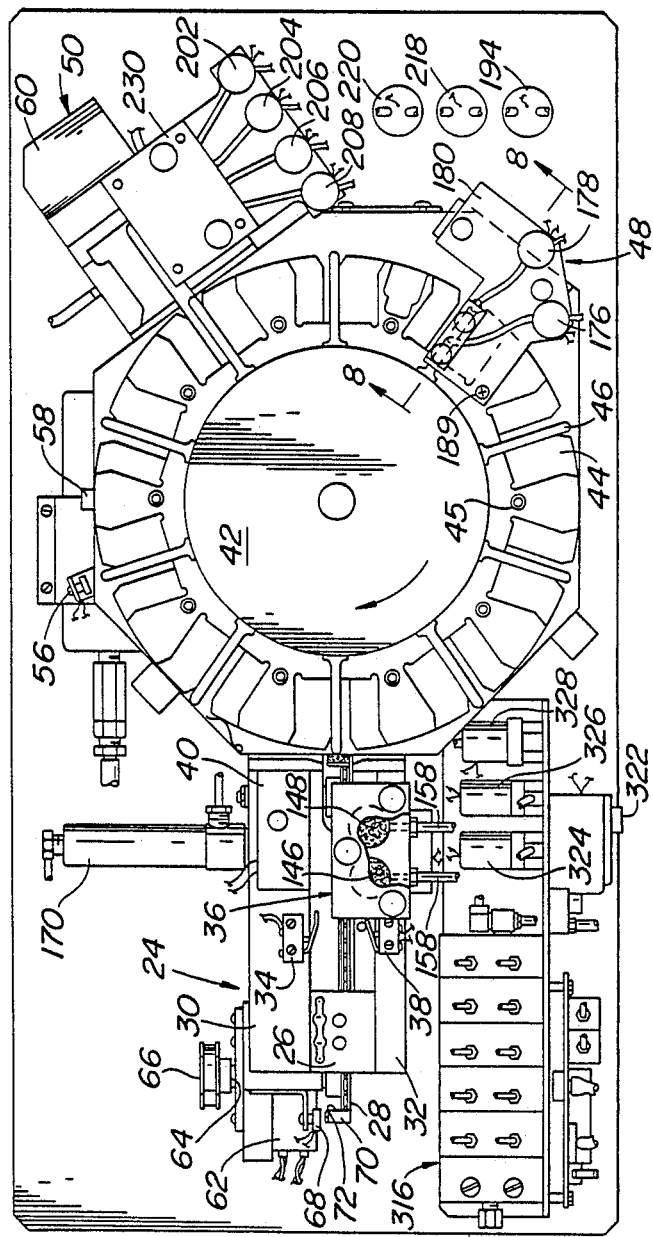
FIG. 2 is a top plan view of the major operational components of the invention.

Referring now to FIG. 2, the major components of analyzer 10 are shown in detail. A conveyor 24 is provided for receiving sample cells 26 from the operator after a whole blood or plasma sample has been place thereinto. Conveyor 24 comprises a conveyor chain 28 and guide rails 30 and 32, which define a path along which samples cells 26 are moved by conveyor chain 28. Conveyor chain 28 is driven by a stepping motor 62.

Mounted on guide rail 30 is a first microswitch 34 which is mounted to detect passage of either a plasma or whole blood sample cell 26 along the conveyor 24 toward the indexing/filtration station 36. Mounted on guide rail 32 is a second microswitch 38. Microswitch 38 is elevated with respect to microswitch 34, and is activated only when a whole blood cell is present on the conveyor. It will be understood that any other means of detecting sample cells 26 on conveyor 24, such as by using optical detectors, may be used without departing from the invention.

Figure 3:
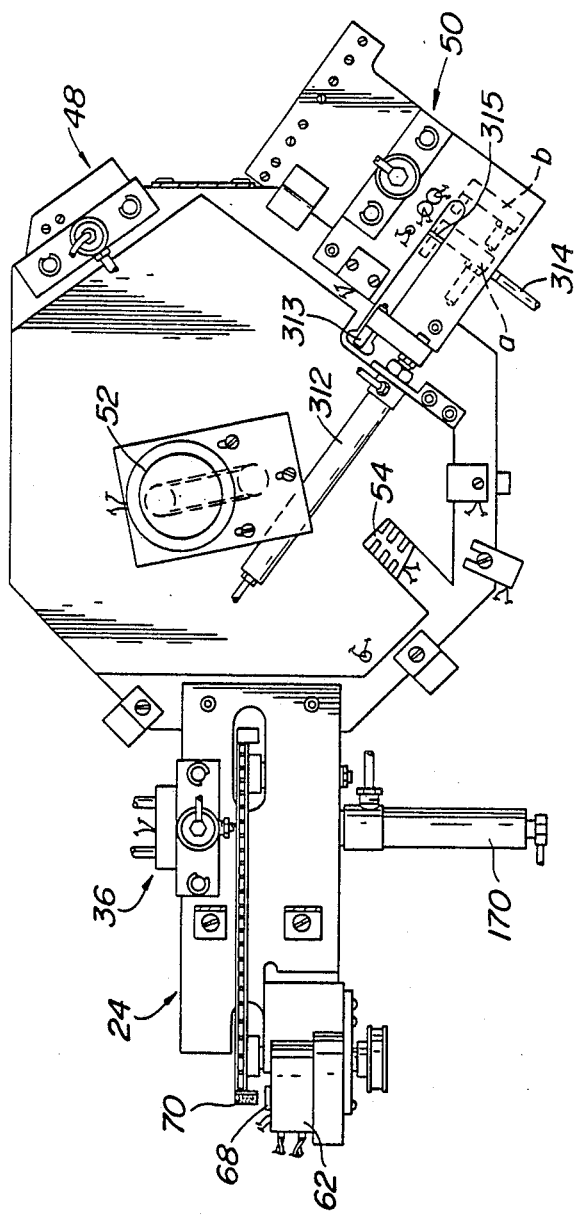
FIG. 3 is a bottom plan view of the components shown in FIG. 2.

At the end of conveyor 24 is located a carousel 42. Carousel 42 comprises a plurality of sample cell receiving stations 44 located around the circumference of carousel 42. Associated with each sample cell receiving station 44 is a resilient spring finger 46 which serves to hold the sample cell in position as carousel 42 moves the sample cell to the pre-test reagent delivery station 48 and test station 50, as required. Carousel 42 is driven by a stepping motor 52, as best seen in FIG. 3. Carousel 42 is also heated by an electric resistance heater 54 which heats carousel 42, and all sample cells 26 on carousel 42, to a temperature of 37° C. This insures that all testing will be done at 37° C.

Referring again to FIG. 2, angular position of carousel 42 is detected by position sensor 56, which in the preferred embodiment may be a Hall effect sensor, which detects when magnet 58 moves past sensor 56. The operation of Hall effect sensors is well understood, and need not be described here in detail. Likewise, indexing of carousel 42 using a stepping motor and position sensor is also well known, and need not be described in detail. Of course, those skilled in the art will recognize that any other method of sensing and controlling angular position of carousel 42, such as using a shaft encoder and an optical sensor, may be substituted for a Hall effect sensor without departing from the scope of the invention.

Carousel 42 rotates in the clockwise direction, as shown by the arrow in FIG. 2. Thus, carousel 42 receives a sample cell 26 from conveyor 24, and conveys them to pre-test reagent delivery station 28, where pre-test reagents are delivered to cell 26 if required. Pre-test reagent delivery station 48 is located above sample cell receiving stations 44 on carousel. From there, sample cell 26 is delivered and transferred to test station 50, where actual testing of the sample is conducted. Test station 50 is located adjacent carousel 42. After the test is completed, sample cell 26 is removed from test station 50 and discharged into waste bin 22 via chute 60.

As best seen in FIG. 2, conveyor 24 is driven by an electric stepping motor 62, which is coupled to the conveyor drive shaft 64 via transmission 66. The exact manner in which conveyor chain 28 is driven is not critical to the operation of the present invention. Linear position of conveyor chain 28, and therefore linear position of any sample cell 26 which may be present on conveyor 24, is determined by a second Hall effect sensor 68 which senses the passage of magnets 70 located at periodic intervals along conveyor chain 28. As with carousel 42, any known type of conveyor position sensor may be used to determine linear position of conveyor chain 28.

Associated with each magnet on conveyor 28 is a sample cell engaging member 72 which engages sample cells 26 and moves them from the inlet end of conveyor 24 to indexing/filtering station 36 and then to carousel 42.

II. Sample Cells

The apparatus 10 of the present invention is designed to perform coagulation testing on blood plasma. Either blood plasma or whole blood may be used. If whole blood is used as the starting material apparatus 10 has the capability of extracting the plasma from the whole blood, so that a prior separation operation, such as centrifugation, need not be carried out. If blood plasma has already been separated from a whole blood sample, the separation of plasma from whole blood need not be performed by apparatus 10 and testing will proceed on the plasms sample. Regardless of whether whole blood or blood plasma is used as the starting material, all testing is performed on blood plasma.

The present invention employs two novel sample cells, a plasma cell for use when a plasma sample has already been separated from whole blood, and a whole blood cell for use when whole blood is used as the starting material. In both cases, the sample cell will contain duplicate plasma specimens, so that all testing is performed simultaneously in duplicate.

A plasma cell is illustrated in FIGS. 13-16. The plasma cell is designated generally by reference numeral 74. Plasma cell 74 consists of two parts, slide portion 76 and body portion 78. Slide portion 76 is also used in the whole blood cell, to be described hereinafter.

Figure 13:
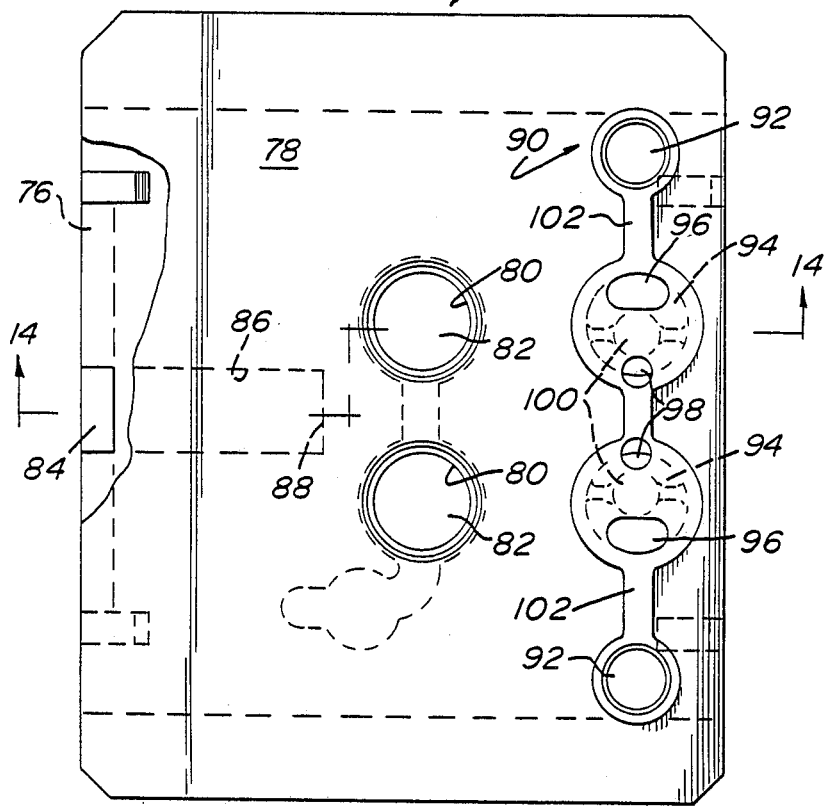
FIG. 13 is a top plan view of a plasma cell before aliquoting.
Figure 14:
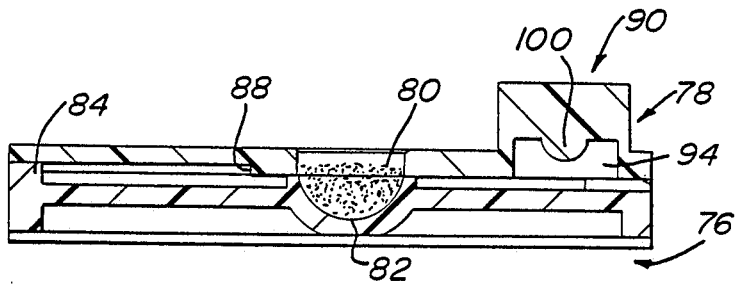
FIG. 14 is a sectional view of the plasma cell taken along the lines 14—14 in FIG. 13.

Plasma cell 74 as shown in FIG. 13 is configured for receiving a plasma sample, whereby body portion 78 and slide portion 76 are in alignment on all four sides. In that position, openings 80 in body portion 78 are aligned with hemispherical wells 82 in slide portion 76. Wells 82 preferably have a volume of 25 microliters. Because of the small volume of wells 82, only a very small amount of plasma, and therefore only a very small amount of test reagent, is required for testing. This results in a large saving in expensive biological test reagents. Thus, the present invention is relatively inexpensive to operate.

A blood plasma sample is dispensed into each of wells 82 through openings 80, for example by a transfer operation. This operation is done manually by a laboratory technician. Alternatively, as will be recognized by those of ordinary skill in the art, the transfer operation may be done automatically, further receiving operator intervention. After a plasma sample has been dispensed into plasma cell 74, cell 74 is placed on the inlet end of conveyor 24. Other than placing the sample cell 26 with the sample on conveyor 24 and entering the appropriate instructions via keyboard 12, no manual operations need be performed with the apparatus of the present invention.

Body portion 78 and slide portion 76 of plasma cell 74 are movable relative to each other. When viewed as in FIG. 13, slide portion 76 may move to the left relative to body portion 78 without restriction. Slide portion 76 may also move to the right relative to body portion 78, by movement in the rightward direction is limited by stop 84 on slide portion 76, which moves in a channel 86 on body portion 78. Channel 86 has an end wall 88 which in cooperation with stop 84 limits movement of slide portion 76 in the rightward direction as viewed in FIG. 13.

Body portion 78 of plasma slide 74 has a raised molded portion 90. Raised molded portion 90 supports cavities 92, which cooperate wiht locating pins on the pre-testing reagent delivery station 48 and test station 50, to be described in greater detail below. Molded portion 90 also supports two downwardly opening cylindrical cavities 94, which are substantially open at their bottom end, i.e., the end which faces slide portion 76. Cylindrical cavities 94 are substantially closed at their opposite end, with the exception of two openings 96 and 98 respectively. Opening 96 is generally eliptical in shape and permits reagent to be injected into the cell 74, as will be described in greater detail below. Opening 98 is a vent opening, which permits air to be vented as reagent is injected. Opening 98 may be eliminated for ease of molding body portion 78. Opening 96 is sufficient for proper venting.

Projecting downwardly from the substantially closed end of cylindrical cavities 94 are substantially cylindrical projections 100. Projections 100, also referred to herein as "light pipes" 100, are important to the optical inspection of the test sample, to be described in greater detail below.

Slide portion 76 and body portion 78 of cell 74 are preferably constructed of a clear polystyrene material or an equivalent. Slide portion 76 and body portion 78 of cell 74 are substantially transparent.

Cavities 92 and 94 of molded portion 90 are connected together by molding ribs 102, which facilitate fabrication of body portion 78.

Figure 19:
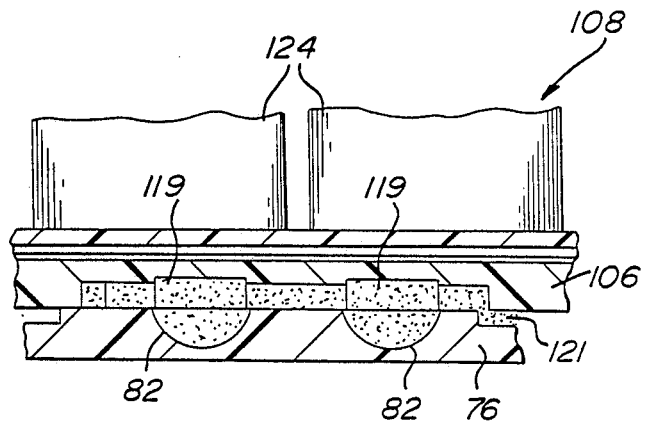
FIG. 19 is a sectional view of the whole blood cell taken along the lines 19—19 in FIG. 18.
Figure 17:
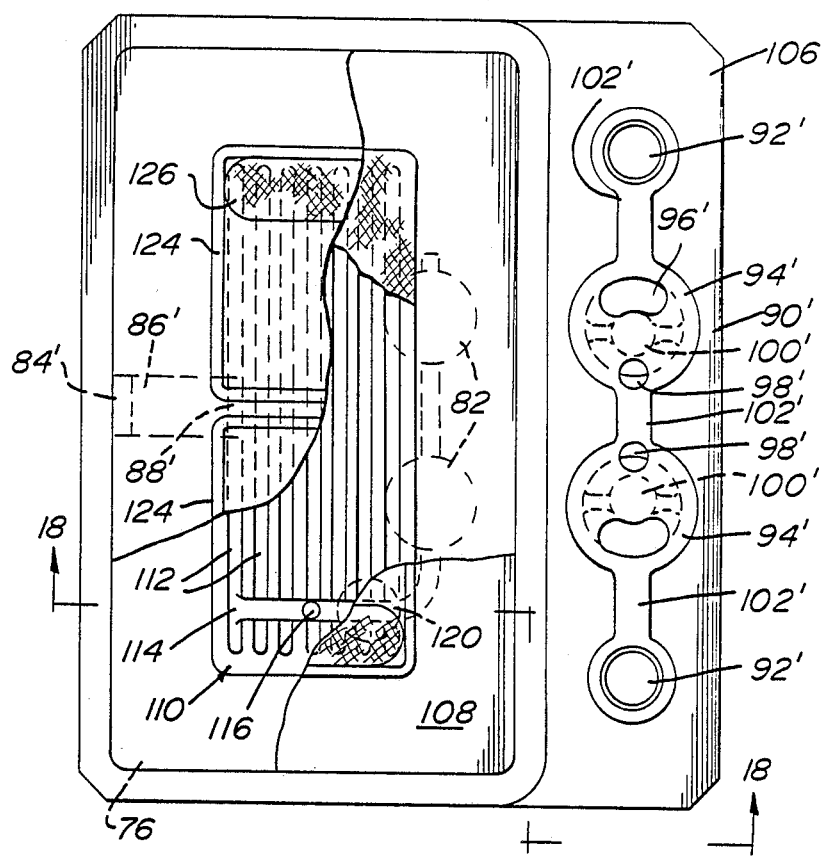
FIG. 17 is a top plan view and partial section view of a whole blood cell before aliquoting.
Figure 18:
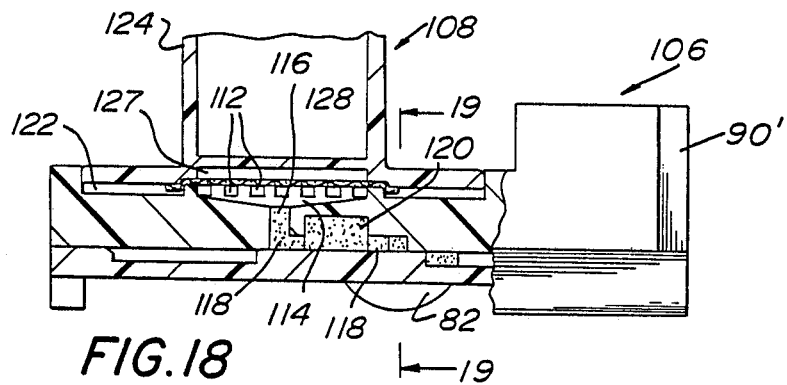
FIG. 18 is a sectional view of the whole blood cell taken along the lines 18—18 in FIG. 17.

Whole blood cell 104, which is used when whole blood is used as the starting material, is illustrated in FIGS. 17-19. Whole blood cell 104 comprises slide portion 76, body portion 106 and reservoir portion 108. Slide portion 76 is identical to slide portion 76 of plasma cell 74. Body portion 106 comprises a molded portion 90', which contains structure substantially identical to that in molded portion 90 of body portion 78 of plasma cell 74. Thus, molded portion 90' contains cavities 92' which cooperate with locating pins at the pretest reagent dispensing station 48 and test station 50. Molded portion 90' also includes two cylindrical cavities 94', each of which have a reagent inlet opening 96' and vent opening 98', all substantially as described in connection with the corresponding elements in the plasma cell body portion 78. Projecting downwardly from the substantially closed cylindrical cavities 94' are light pipes 100'. Molding ribs 102' connect cavities 92' and 94'.

In addition tomolded portion 90', body portion 106 has a plasma collection area 110. Plasma collection area 110 comprises a number of longitudinal channels 112 interconnected by and which communicates with a transverse channel 114. Channels 112 and 114 collect filtered plasma from whole blood placed in reservoir portion 108, as will be described in Section III below. An opening 116 is provided in channel 114 through which collected plasma may flow into wells 82 in slide portion 76. On the underside of body portion 106 beneath the plasma collection area 110, and communicating with opening 116, is plasma channel 118. Plasma channel 118 allows collected plasma from channels 112 and 114 which has flowed through opening 116 to flow into sample wells 82 on slide portion 76. Located in channel 118 is a bubble trap 120 to prevent any bubbles in the collected plasma from being carried into sample wells 82. Body portion 106 also includes cylindrical cavities 119, which act as secondary bubble traps to prevent any trapped air in the collected plasma from reducing the sample volume delivered to sample cells 82, and which also act as excess material traps. Excess material is sheared off when slide portion 76 is indexed from the first position to the second position.

Reservoir portion 108 of whole blood cell 104 is located in recess 122 in body portion 106 (see FIG. 19) and comprises twin reservoirs 124 which overlie and align with plasma collection area 112 of body portion 106. Reservoirs 124 are substantially rectangular in shape and are open at the top. The bottom ends of reservoirs 124 are substantially closed except for generally rectangular openings 126. The bottom ends of reservoirs 124 are slightly raised with respect to the side walls of reservoirs 124 so as to form a channel 127 (see FIG. 18) below reservoirs 124. Located below reservoirs 124 and between reservoir portion 108 and plasma collection area 110 of body portion 106 is a filter membrane 128. Reservoirs 124 are in communication via openings 126 and channel 127 formed below reservoirs 124 and above filter membrane 128. The filter membrane 128 may be a polycarbonate sheet having a plurality of pores, pore density being approximately $3 \times 10^7$ pores per square centimeter and maximum pore size being approximately 0.6 micron. Filter membrane 128 separates plasma from the whole blood placed in one of reservoirs 124, as will be described in greater detail in Section III.

III. Indexing/Filtering Station

Indexing/filtering station 36 performs two major functions: (1) when whole blood is used as the starting material, the indexing/filtering station 36 causes the blood plasma to be extracted from the whole blood and (2) indexes slide portion 76 of either a plasma cell or a whole blood cell to provide a precise plasma sample volume for testing. A description and operation of the indexing/filtering station 36 in relation to the extraction of plasma from whole blood will be described first.

Figure 4:
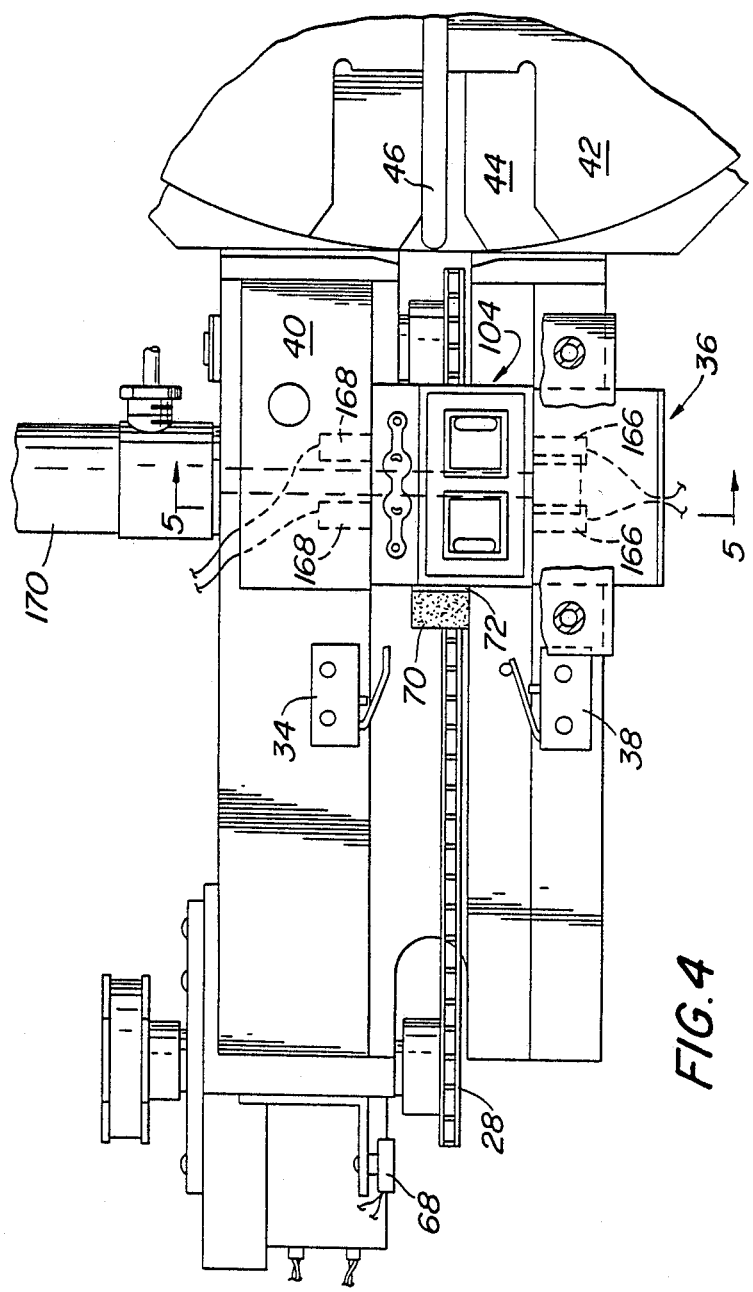
FIG. 4 is a detailed top plane view of the cell conveyor and the indexing/filtration station.
Figure 5:
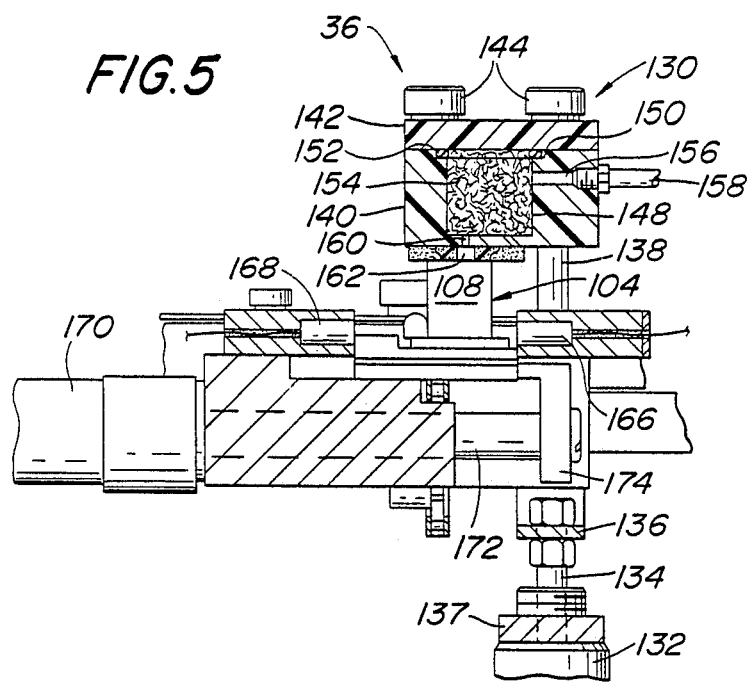
FIG. 5 is a section of the indexing/filtration station taking along the lines 5—5 in FIG. 4 in the filtration position prior to indexing of a sample cell.
Figure 6:
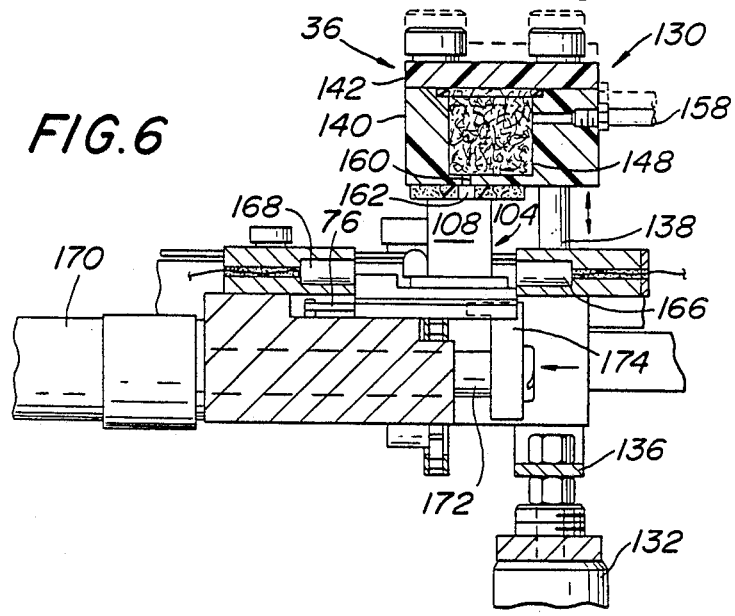
FIG. 6 is a section of the indexing/filtration station taken along the lines 5—5 of FIG. 4, and showing indexing of a sample cell.

As shown in FIGS. 4-6, a whole blood cell 104 is shown in position at the indexing/filtering station 36. Whole blood cell 104 is transported to position at indexing/filtering station 36 by conveyor 24. Indexing/filtering station 36 comprises a movable head portion 130. Head portion 130 is reciprocally movable in a vertical direction by a pneumatic cylinder 132. Pneumatic cylinder 132 is a double-acting cylinder. Cylinder 132 has a piston (not visible) to which is attached a piston shaft 134. The free end of piston shaft 134 is fastened to bracket 136, which is fixed to conveyor 24. A bracket 137 is attached to cylinder 132 and is movable therewith. Fastened to bracket 137 are posts 138 (only one post is visible in FIGS. 5 and 6). Cylinder 132 moves up and downn in concert with head portion 130, while piston shaft 134 remains fixed to bracket 136.

Head portion 130 is mounted on the ends of posts 138 furthest from bracket 137. Head portion 130 comprises a body portion 140 and a cover portion 142. Cover portion 142 is removably attached to body portion 140 by fasteners 144. Fasteners 144 may, for example, be thumb screws or the like. Within body portion 140 are two chambers, a left chamber 146 and a right chamber 148 (see FIG. 2). Only right chamber 148 is illustrated in FIGS. 5 and 6. Chambers 146 and 148 are preferably cylindrical, but may have any other shape as well. Each chamber has an increased diameter portion 150 at its top. The increased diameter portion is adapted to seat an O-ring 152 so as to form a tight seal between cover portion 142 and the chamber. A filtering material 154 may be located in the chambers to prevent whole blood from entering air passageways 156. Passageways 156 form air inlets into chambers 146 and 148. Air is supplied to and removed from chambers 146 and 148 by means of passageways 156 and tubing 158. Chambers 146 and 148 have air passages 160 in their bottom surfaces.

Below body portion 140, and attached thereto, is a resilient seal 6162. Seal 162 has an opening 164 through which air from chamber 148 may pass into reservoir portion 108 of whole blood cell 104. Seal 162 is substantially impermeable to air, so that air flows only through opening 164. Seal 162 is resilient so as to form a tight seal between body portion 140 and reservoir 108 of whole blood cell 104.

When a whole blood cell 104 is first moved into position at indexing/filtering station 36, head portion 130 is at its upper position, shown in phantom in FIG. 6. After whole blood cell 104 is in place, head portion 130 is moved downwardly by pneumatic cylinder 132 until seal 162 rests on top of reservoir portoin 108 of whole blood cell 104. Whole blood cell 104 is positioned such that left chamber 146 is located above one reservoir 124 and right chamber 148 is located above the other reservoir. Air at a nominal pressure of 3 psi is alternately admitted into and bled from left chamber 146 and right chamber 148 via tubing 158. That is, left chamber 146 and right chamber 148 are alternately pressurized and vented, respectively. This causes whole blood to be moved from one reservoir 124 to the other reservoir 124 through openings 126 at the bottoms of the reservoirs and through channel 127 past filter membrane 128 in reservoir portion 108 of whole blood cell 104. As the whole blood is moved back and forth from one reservoir to the other past filter membrane 128, plasma is filtered from the whole blood through filter membrane 128 and collected in channels 112 and 114 and directed through opening 116 to slide portion 76, where it is ultimately collected in cavities 119 and plasma wells 82 in slide portion 76. Any excess plasma is vented through passageway 121 formed between slide portion 76 and body portion 106.

In order to prevent air bubbles from being trapped in the filtered plasma, some portion of the whole blood is retained in each reservoir 124 at all times, so that during cycling of the whole blood from one reservoir to the other, neither reservoir is permitted to run dry. The decreasing blood level in each reservoir is detected optically. A light source 168, which may be a light emitting diode or other light source, is located on one side of whole blood cell 104. On the opposite side of whole blood cell 104 is located a photodetector 166. A separate light source 168 and photodetector 166 are provided for each reservoir 124. Light source 168 and photodetector 166 are aligned so that the optical line-of-sight is through the lower portion of reservoirs 124. When the whole blood level in a reservoir drops below the line-of-sight of light source 168 and photodetector 166, light from light source 168 strikes photodetector 166, and causes photodetector 166 to generate an output signal. The output signal is detected by level detector electronics. Occurrence of the signal stops the flow of air into chamber 146 or 148 associated with that reservoir and simultaneously vents that chamber to atmosphere and admits air into the opposite chamber, thereby reversing the direction of whole blood flow. Thus, some whole blood always remains in each reservoir 124, and there is no possibility of introducing air bubbles into the plasma through filter membrane 128.

After filtering of the whole blood is complete, pneumatic cylinder 170 is activated, which causes an associated piston shaft 172 to move to the left as viewed in FIGS. 5 and 6. At the freee end of piston shaft 172 is located a bracket 174 which is aligned opposite slide portion 76 of whole blood cell 104. Thus, as shaft 172 and bracket 174 move to the left, slide portion 76 is moved to the left relative to body portion 106 until stop 84 contacts end wall 88' of channel 86' in body portion 106 of whole blood cell 104. When indexing is complete, piston shaft 172 moves to the right so that bracket 174 clears whole blood cell 104. Simultaneously, head 130 is moved to its uppermost position by cylinder 132.

In the event that plasma is used as the starting material rather than whole blood, a plasma cell 74 containing the plasma sample is placed on conveyor 24. Conveyor 24 moves plasma cell 74 into position at indexing/filtering station 36. Since the sample is plasma, no filtering operation need be done. Thus, once plasma call 74 is in position at indexing/filtering station 36, only pneumatic cylinder 170 is activated, which moves slides portion 76 relative to body portion 78 until stop 84 contacts end wall 88 of channel 86 in body portion 78. When indexing is complete, piston shaft 172 moves to the right so that bracket 174 clears plasma cell 74. Simultaneously, head 130 is moved to its uppermost position by cylinder 132.

At this point, operation of the system is the same regardless of whether a whole blood or plasma was used as the starting sample. Accordingly, further description will be directed to operation with a plasma cell 74.

Figure 15:
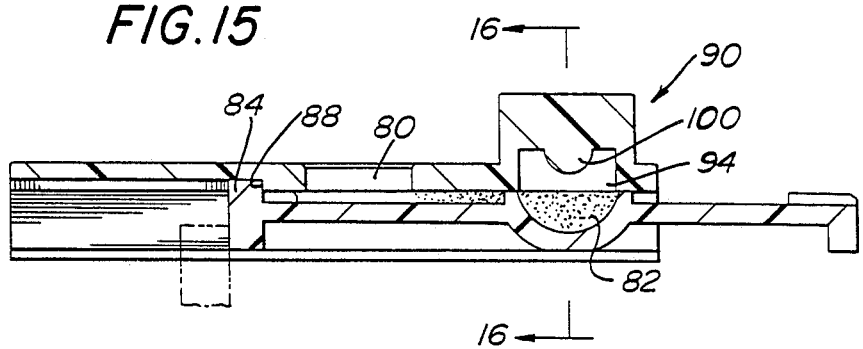
FIG. 15 is a sectional view of a plasma cell after aliquoting.
Figure 16:
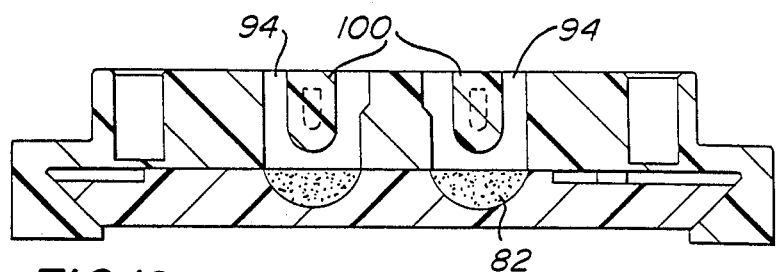
FIG. 16 is a sectional view of the plasma cell after aliquoting taken along the lines 16—16 in FIG. 15.

Referring now to FIGS. 15 and 16, plasma cell 74 is shown in what may be termed the indexed position. In this position, cylindrical cavities 94 are located over and coaxial with plasma well 82. Cylindrical cavities 94 and plasma wells 82 cooperate to form test chambers. Movement of slide portion 76 relative to body portion 78 not only brings cavities 94 into alignment with plasma wells 82 to form test chambers, buy any excess plasma introduced into the plasma cell is sheared off by the lower surface of body portion 78. This results in very precisely controlled volumes of plasma remaining in plasma wells 82. This eliminates the need for precise volumetric dispensing of the plasma sample, and eliminates the possibility of having a sample size which is larger than necessary and which may yield inaccurate test results.

In will be seen that, by viture of the novel configuration of plasma cell 74 and whole blodd cell 104, two individual test chambers are formed by the two plasma wells 82 in slide portion 76 and the two cylindrical cavities 94 or 94' in plasma cell body portion 78 or whole blood cell body portion 106, respectively. This permits testing of plasma samples to be done in duplicate. By performing the tests in duplicate, a greater degree of accuracy and control is achieved. The duplicate test results can also be averaged, which smoothes out inevitable variations in test results which occur when performing biological testing.

After indexing, the plasma cell 74 is now ready to be placed onto carousel 42 by conveyor 24 for further processing. When carousel 42 is ready to receive a sample cell, carousel stepping motor 52 advances carousel 42 to move a vacant sample cell receiving station 44 opposite the outlet end of conveyor 24. Then, the conveyor stepping motor 62 is directed to advance to its starting position. This action causes a sample cell at the indexing/filtering station 36 to advance onto the sample cell receivin station 44 on carousel 42. Once on carousel 42, the sample cell and the sample in contains are allowed to equilibrate to 37° C., at which temperature all further processing is carried out.

The plasma cell 74 is now ready to be moved to pretest reagent delivery station 48 if required.

IV. Pre-test Reagent Delivery Station

If the test to be performed on the plasma sample requires introducing a pre-test reagent into the plasma, plasma cell 74 is moved by carousel 42 to pre-test reagent delivery station 48.

Figure 7:
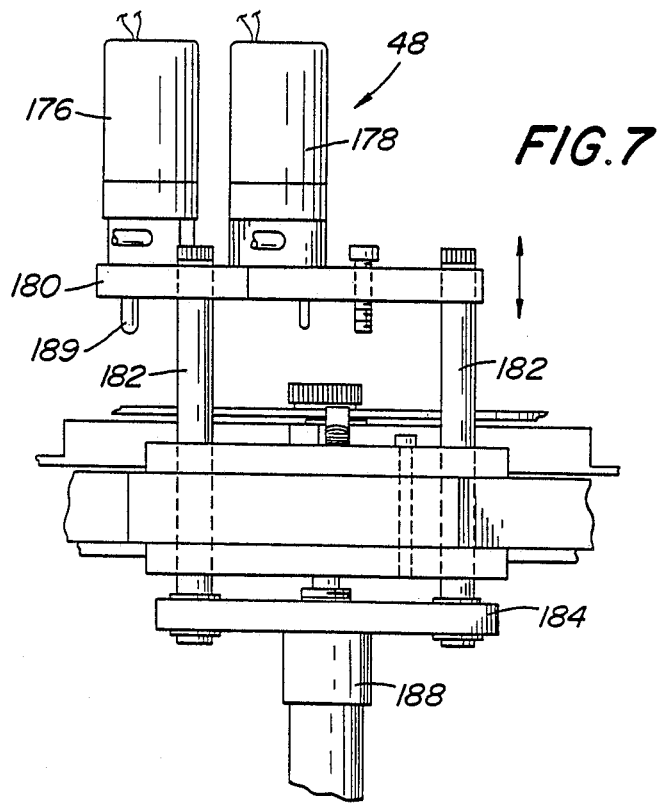
FIG. 7 is a side elevation view of the pre-test reagent delivery station.
Figure 8:
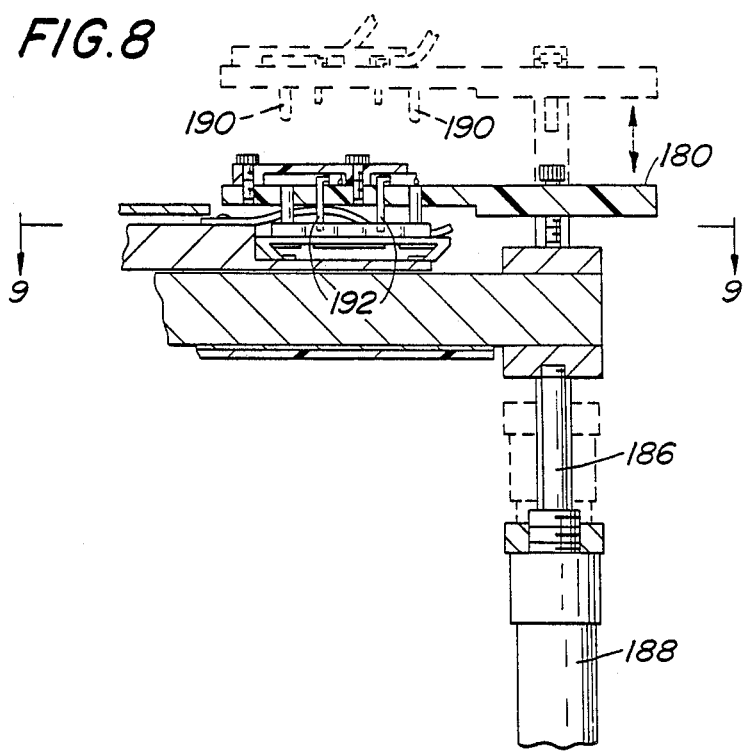
FIG. 8 is a sectional view of the pre-test reagent delivery station taken along the lines 8—8 in FIG. 2.

Pre-test reagent delivery station 48 is shown in FIGS. 7 and 8. Pre-test reagent delivery station comprises two solenoid valves 176 and 178 for controlling delivery of reagent into the test chamber on plasma cell 74. Solenoid valves 176 and 178 are mounted on a plate 180. For clarity, solenoid valves 176 and 178 are omitted from FIG. 8. However, it is believed that the operation of pre-test reagent delivery station 48 can be understood completely by reference to FIGS. 7 and 8.

Plate 180 is vertically reciprocable by means of posts 182 which are fastened to bracket 184 connected to the piston 186 of a pneumatic cylinder 188.

Figure 9:
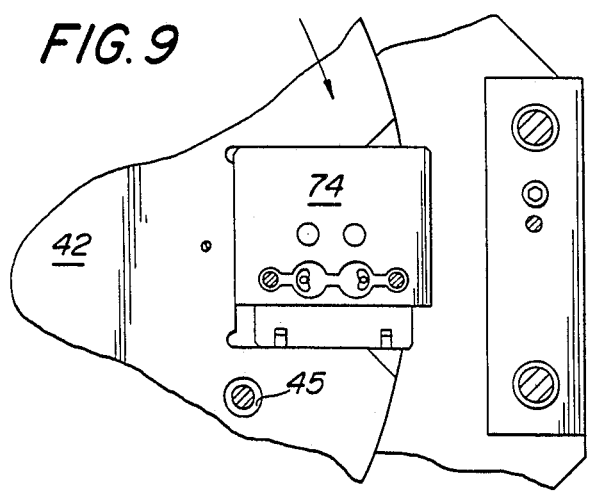
FIG. 9 is a top plan view of a sample cell at the pre-test reagent delivery station taken along the lines 9—9 in FIG. 8.

As a plasma cell 74 is moved into position at pre-test reagent dispensing station 48, plate 180 is at its highest position. This allows plasma cell 74 to be easily moved into place. Once plasma cell 74 is in place, plate 180 is moved downwardly by piston 186 and cylinder 188. A downwardly projecting carousel locating pin 189 on plate 180 enters the carousel locating holes 45 (FIG. 9) adjacent the sample cell receiving station 44 in which plasma cell 74 is situated. As plate 180 continues its downward motion, downwardly projecting sample cell locating pins 190 enter locating cavities 92 in plasma cell 74 so that cell 74 is precisely aligned with respect to the pre-test reagent delivery station 48. Also, downwardly projecting nozzles 192 enter reagent inlet openings 96 in plasma cell 74. Nozzles 192 deliver reagent from reagent bottle 194 (see FIG. 2). Flow of pre-test reagent from reagent bottle 194 is controlled by solenoid valves 176 and 178. The reagent delivery system is described in greater detail in Section VI.D. below. Although delivery of only one reagent is described, it will be apparent that provision for delivery of any number of pre-test reagents may be made without departing from the invention.

After the proper amount of pre-test reagent is delivered into the test chambers in plasma cell 74, the cell is allowed to incubate for a preselected time until actual testing is to be performed. When the incubated sample is ready for testing, it is moved by carousel 42 to test station 50 and transferred to test station 50 by pneumatic cylinder 312 and pawl 313. Pawl 313 is advanced to position a (shown in phantom in FIG. 3). Movement of pawl 313 is limited by pin 315, which is operated by pneumatic cylinder 314, so that plasma cell 74 is located in proper position at test station 50. After plasma cell 74 is in position, pawl 313 is retracted by cylinder 312 to its initial position.

V. Test Station

Figure 12:
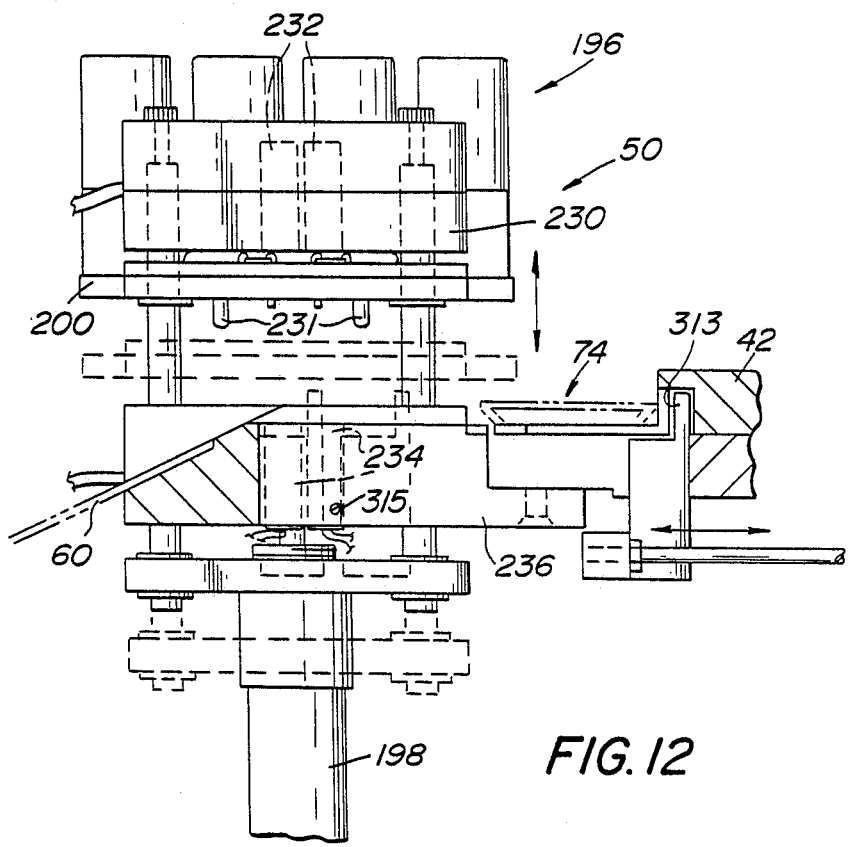
FIG. 12 is a side elevational view of the test station taking along the lines 12—12 in FIG. 10.

Test station 50 is shown in FIGS. 10 through 12. Test station 50 is maintained at 37° C. by a separate heater (not shown). Test station 50 comprises a head portion 196 which is movable vertically by means of a pneumtic cylinder 198 and piston arrangement substantially identical to that described for the indexing/filtering station and the pre-test reagent delivery station. Head portion 196 comprises a plate 200 on which are mounted solenoid valves 202, 204, 206 and 208. Each solenoid valve has associated with it a nozzle 210, 212, 214 and 216, respectively. Nozzles 210 and 216 dispense a first test reagent from reagent bottle 218 (see FIG. 2). Nozzles 212 and 214 deliver a different reagent from reagent bottle 220 (see FIG. 2). Reagent bottles 194, 218 and 220 are maintained at 2° to 8° C. by a thermoelectric cold module (not shown). Provision may also be made for magnetically stirring the contents of reagent bottles 194, 218 and 220, as is well known in the art. The particular reagent required is determined in accordance with the particular test to be performed on the plasma sample. Although provision for delivery of two reagents is described, those skilled in the art will recognize that provision can be made for delivery of any number of reagents without departing from the scope of the present invention.

Nozzles 210, 212, 214 and 216 are connected to solenoid valves 202, 204, 206 and 208 via flexible tubing 222, 224, 226, and 228 and thermally conductive tubing 223, 225, 227 and 229, respectively. A heater (not shown) in head 230 is in thermal contact with tubing 223, 225, 227 and 229 in order to maintain a dosage of reagent at 37° C., so that introduction of the reagent into the plasma sample will not change the temperature of the plasma sample.

The length of flexible tubing 222, 224, 226 and 228 and thermally conductive tubing 223, 225, 227 and 229 is chosen such that the liquid volume in the thermally conductive tubing between the valve and the nozzle orifice is equal to the desired volume of liquid to be delivered for a particular test.

Located above nozzles 210, 212, 214 and 216 and their associated tubing is optical inspection head 230. Optical inspection head includes a pair of light sources 232 located above and to the inside of nozzles 210 and 212, and nozzles 214 and 216. See FIG. 12. Located below and in axial alignment with light sources 232 are a pair of photodetectors 234 to detect light transmitted through the plasma sample. Photodetectors 234 are mounted in a plate 236 which is fixed in the plane of carousel 42.

The axes of light sources 232 and photodetectors 234 are located so as to coincide with the axes of light pipes 100 in plasma cell 74 when placed in position by pawl 313. Thus, optical detection of clothing time is observed by passing light through the test sample via light pipes 100 in a vertical direction.

After plasma cell 74 is placed in position at test station 50, optical inspection head 230 is moved downwardly by pneumatic cylinder 198. Downwardly projecting locating pins 231 on head 230 enter locating cavities 92 in plasma cell 74 so that cell 74 is precisely aligned with respect to test station 50. That is, cell 74 is positioned so that the axes of light sources 232 and photodetectors 234 are precisely aligned with the axes of light pipes 100. At the same time, nozzles 210, 212, 214 and 216 enter openings 96 on plasma cell 74.

When the head 230 is in its lowest position, a sufficient amount of test reagent is injected by nozzles 210 and 216 or nozzles 212 and 214, as required, in order to raise the level of the sample in the test chambers in plasma cell 74 so that light pipes 100 become immersed in the sample liquid. Thus, light from light sources 232 enters the sample from light pipes 100, eliminating an air/liquid interface. This eliminates any potential problems due to reflection of the light from the surface of the sample, and also eliminats any problems due to bubbles on the surface of the sample which may have been caused by introduction of the sample or introduction of the reagents into the test chamber.

The cylindrical shape and rounded end of light pipes 100 serves to disperse the light from light sources 232 through a full 360° in the test chambers. Thus, the entire sample in the test chambers is illuminated and observation of the entire sample can be made. This yields highly accurate and precise test results, results which are not obtained by known optical inspection systems.

At this point, optical inspection is performed as described in detail in Section VI.E. below.

After optical inspection is completed, head 230 is moved to its uppermost position by cylinder 198. Plasma cell 74 is ready to be ejected. If another test is to be run, carousel 42 moves the next sample cell into position opposite test station 50, and the next sample cell is moved onto test station 50 by pawl 313. Movement of the next sample cell onto test station 50 ejects the previous sample cell from test station 50 onto chute 60, from where the previous sample cell falls into waste bin 22. If no further tests are to be run, pin 315 is retracted by cylinder 314, (see FIG. 3) and pawl 313 is advanced by cylinder 312 to position b (shown in phantom in FIG. 3). Pawl 313 thus ejects the sample cell from test station 50 onto chute 60 for disposal.

Typically, the reagents used for testing are biological reagents. Thus, such reagents will denature after a finite time at 37° C. and will no longer be fresh. It is therefore advantageous to discard reagents which have been at 37°C. for too long a time. For this purpose, a spring-loaded reagent receptacle, not shown, is provided to collect denatured reagent discharged from test station 50 when a sample cell is not present. The spring-loaded receptacle is biased to a position under nozzles 210, 212, 214 and 216 when a cell is not on test station 50. The receptacle is pushed aside out of the way when a sample cell is put onto test station 50.

VI. OPERATION OF ANALYZER SUBSYSTEMS

A. Overall Analyzer Control System

The overall analyzer control system is shown in block diagram form in FIG. 21. The heart of the analyzer control system is microprocessor 238 which controls operation of the analyzer. As inputs, the microprocessor receives signals from the operator keyboard 12; cell detection electronics 240; filter system electronics 242; motion control electronics 244; temperature control electronics 246; reagent delivery electronics 248; and clot detection electronics 250. As outputs, microprocessor 238 drives alphanumeric display 14 and printer 16, and controls operation of the various subsystems mentioned.

Cell detection electronics 240 consist of microswitches 34 and 38 (see FIG. 2). Microswitch 34 detects the presence of any cell on conveyor 24. Microswitch 38 detects whether the cell on conveyor 24 is a plasma cell or a whole blood cell. As noted above, microswitch 38 is elevated with respect to microswitch 34, and is high enough to clear a plasma cell, so that when a plasma cell is placed on converyor 24, microswitch 38 is not activated. Microswitch 38 is activated only when a whole blood cell is placed on conveyor 24. Microswitch 38 is activated when the reservoirs 124 of whole blood cell move past microswitch 38.

The temperature control electronics employ suitable temperature sensors at the test station, test head, and carousel, as well as at a separate cold module (not shown) which is used to cool the reagent bottles 194, 218 and 220. Any suitable conventional temperature control techniques may be used.

B. Motion Control System

Figure 22:
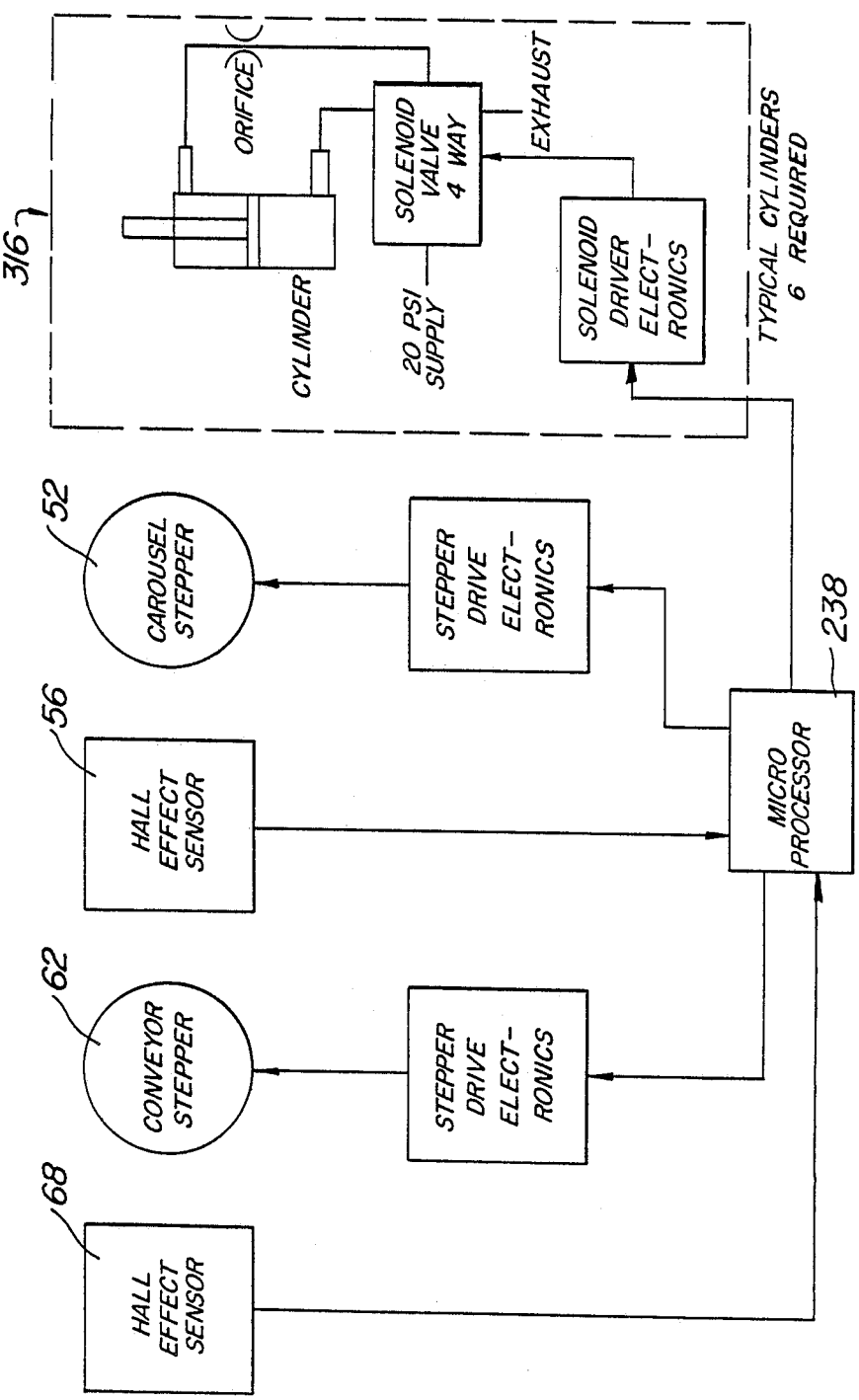
FIG. 22 is a block diagram of the motion control system for the apparatus of the present invention.

The motion control system 244 is shown in greater detail in FIG. 22. The Hall effect sensors 56 and 68 for the carousel and conveyor, respectively, generate inputs to the microprocessor 238. In response to the inputs from the Hall effect sensors 56 and 68, the microprocessor drives the carousel stepping motor and conveyor stepping motor 52 and 62, respectively, through suitable drive electronics. The way in which a stepper motor may be driven is well known, and need not be described in detail here. Microprocessor 238 also controls the operation of solenoid valves, collectively designated by reference numeral 316 (FIG. 22) by means of the solenoid valve driver electronics. Solenoid valves 316 control operation of the pneumatic cylinders associated with the various subsystems, such as the indexing-/filtering station, pre-test reagent delivery station and test station.

Figure 20A:
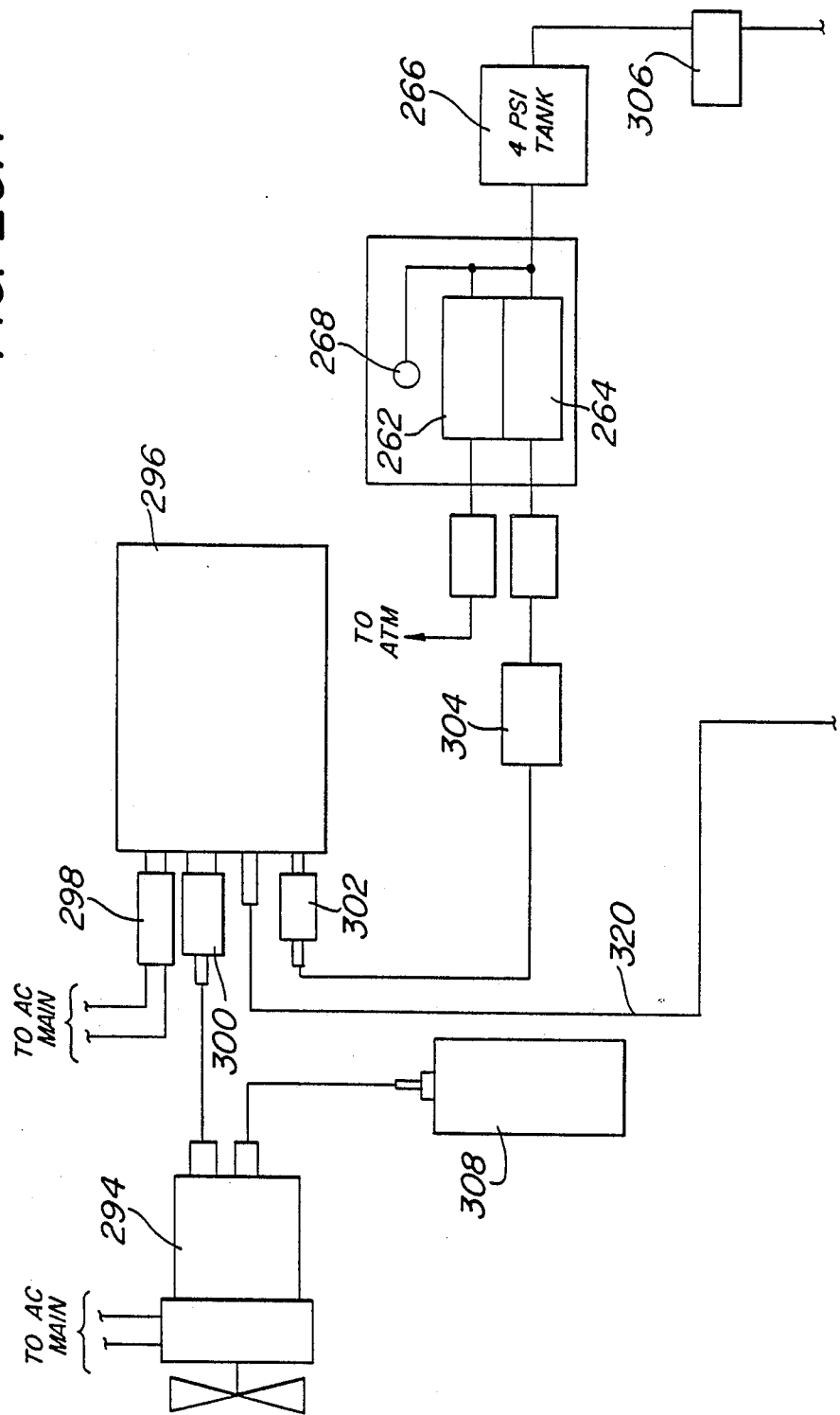

The pneumatic system is shown in greater detail in FIGS. 20A and 20B, and is described in greater detail in Section VI.G. in connection with those FIGS.

C. Filtration Control System

Figure 23:
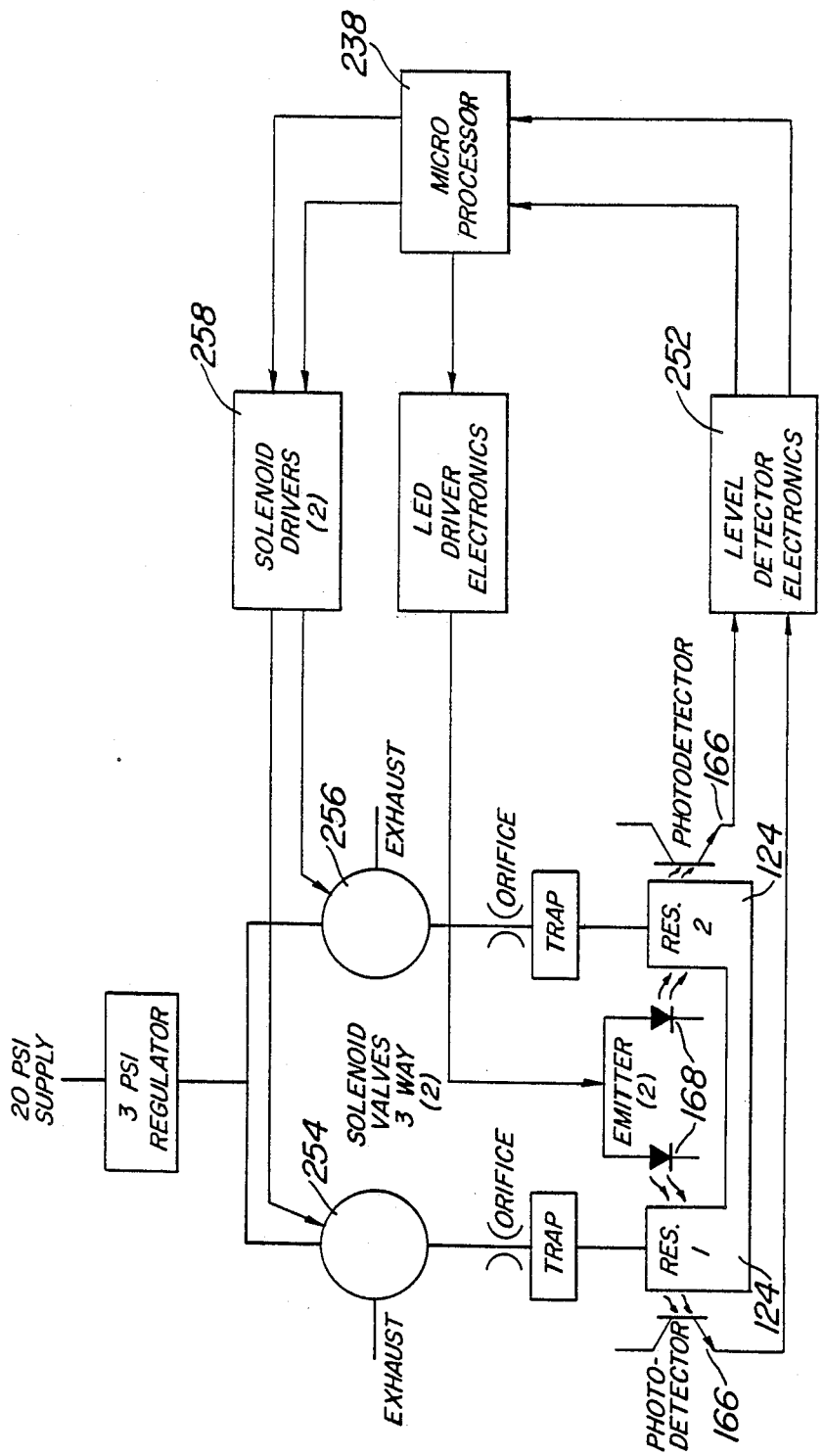
FIG. 23 is a block diagram of the filtration control system for the apparatus of the present invention.

The filtration control system is shown in FIG. 23. As can be seen from FIG. 23, signals from the photodetectors 166 which detect whole blood level in reservoirs 124 have their outputs connected to suitable level detector electronics 252. Conventional level detection techniques may be employed. The output from the level detector electronics is sent to microprocessor 238. In response to the output from the level detector electronics 252, microprocessor 238 drives solenoid valves 254 and 256 by means of solenoid driver circuits 258. Solenoid valves 254 and 256 are three-way valves. When the photodetectors 166 signal level detector electronics 252 that the whole blood level in reservoir 1, for example, has reached a preselected minimum, microprocessor 238 switches solenoid valve 254 from pressure to exhaust and switches solenoid valve 256 from exhaust to pressure. Thus, reservoir 1 ceases to be pressurized and is vented through solenoid valve 254, while reservoir 2 becomes pressurized via valve 256. This causes the whole blood to cease flowing from reservoir 1 to reservoir 2, and reverses the flow of whole blood so that the flow is now from reservoir 2 to reservoir 1. When photodetectors 166 detect that the whole blood level in reservoir 2 has reached a preselected minimum, microprocessor 238 switches solenoid valve 256 from pressure to exhaust and switches solenoid valve 254 from exhaust to pressure. Now, blood no longer flows from reservoir 2 to reservoir 1, but flows in the initial direction. The process is repeated for a number of cycles sufficient to collect the required plasma sample.

D. Reagent Delivery System

Figure 24:
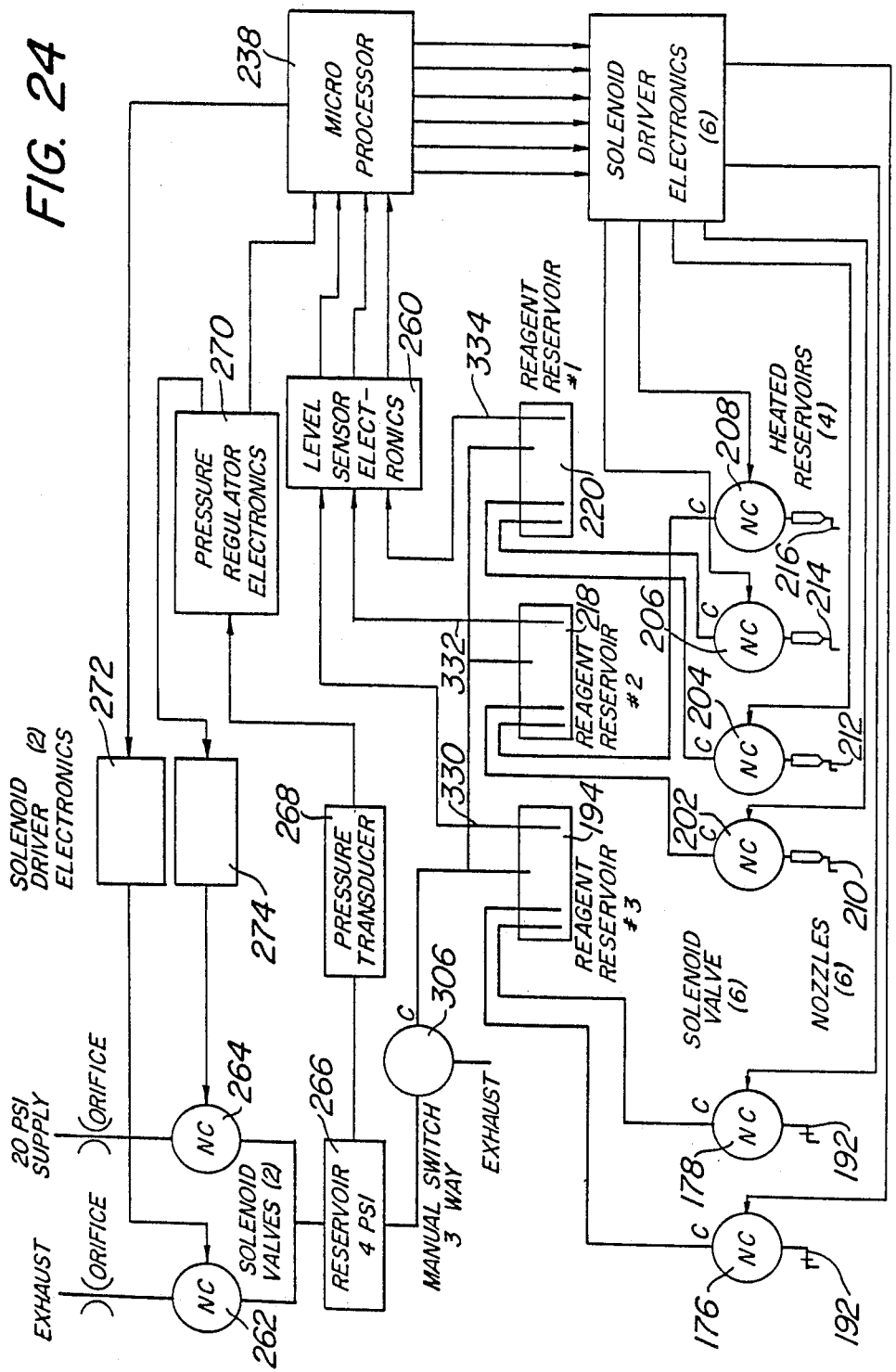
FIG. 24 is a block diagram of the reagent control system for the apparatus of the present invention.

The reagent delivery system is shown in block diagram form in FIG. 24. The level of reagent in reagent bottles 194, 218 and 220 is monitored by electrode level sensors 330, 332 and 334, which are connected to level sensor electronics 260. Level sensor electronics 260 monitor a small current passed through each of the electrodes 330, 332 and 334 to determine whether the bottom of each electrode is immersed in liquid. The manner in which this is accomplished is well known to those skilled in the art. The output of level sensor electronics 260 is sent to microprocessor 238. In the event the level of any reagent in any of the reservoirs falls below a predetermined minimum, microprocessor 238 will signal the operator and, if appropriate, prevent further testing from being attempted until the low reagent is replenished.

As seen in FIG. 24, reagent bottles 194, 218 and 220 are pressurized to approximately 4 pounds per square inch. Solenoid vavles 262 and 264 act as a pressure regulator to regulate the 20 psi used to operate the pneumatic cylinders which move the indexing/filtering station, pre-test reagent dispensing station and test station, down to 4 psi. A 4 psi reservoir 266 holds a sufficient quantity of air to pressurize reagent bottles 194, 218 and 220. A pressure transducer 268 and pressure regulator electronics 270 regulate the operation of solenoid valve 264 through solenoid driver 274. Any suitable pressure transducer 268, pressure regulator electronics 270 and solenoid driver electronics 274 can be used. Solenoid valve 262 is operated by microprocessor 238 through solenoid driver electronics 272.

A precise 4 psi pressure is present in reservoir 266 at the time reagent is dispensed. This is achieved in the following manner. Exhaust valve 262 is opened to exhaust air from reservoir 266 by solenoid driver electronics 272 on command from microprocessor 238. Microprocessor 238 simultaneously monitors the state of pressure regulator electronics 270 to determine when the falling pressure in reservoir 266 will cause pressure regulator electronics 270 to open solenoid valve 264 via solenoid driver electronics 274. When this occurs, microprocessor 238 closes exhaust valve 262 via solenoid drive electronics 272. Microprocessor 238 continues to monitor pressure regulator electronics 270 until it receives indication that solenoid valve 264 has been closed. When this occurs, pressure in reservoir 266 stands precisely at its nominal 4 psi value, and any one or any pair of the dispense valves 176, 178, 202, 204, 206 and 208 can be operated.

Precise metering of reagents dispensed from reagent bottles 194, 218 and 220 is obtained by carefully controlling the time during which any of the solenoid valves 176, 178, 202, 204, 206 and 208 is held open. Because the reagent bottles are pressurized to a precise pressure, reagent will flow through a dispensing nozzle at a precise fixed rate. This rate can be determined for the nozzle diameter by well known formulae. Since the reagent flows at a fixed, known rate, a known amount can be delivered by controlling the time during which the reagent flows. Thus, rather than attempt to monitor and meter reagent flow by sensing the amount of flow, reagent metering is controlled by time of flow.

E. Clot Detection Circuitry

Figure 25:
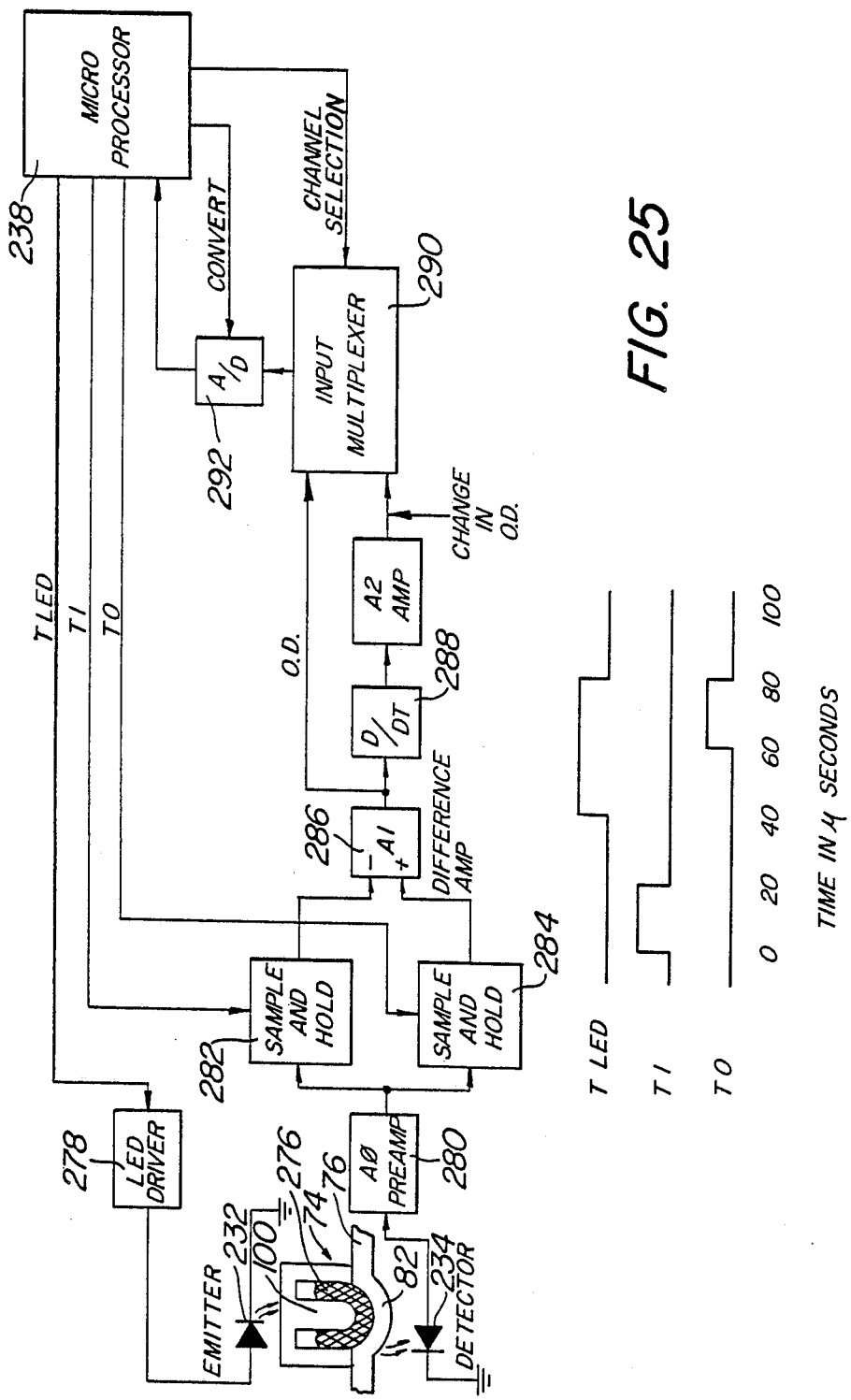
FIG. 25 is a block diagram of the clot detection system for the apparatus of the present invention.

The clot detection circuitry is diagrammed in FIG>25. To the left of FIG. 25, a simplified sketch of the test chamber in a sample cell 74 is shown. As noted above, the liquid level of the test sample 276 is high enough so that light pipe 100 is immersed in sample 276. Light form light source 232 is conducted downwardly through light pipe 100 and from there through sample 276 and sample well 82 to photodetector 234. Light source 232 is preferably a near-infrared LED light source and is driven by microprocessor 238 by means of LED driver 278. Light source 232 is not energized continuously. Rather, light source 23 is pulsed, as by waveform TLED shown in the timing diagram in FIG. 25. Thus, light source 232 is alternately on and off during the test cycle.

The light transmitted through sample 276 is detected by photodetector 234, which, in known manner, generates an electrical signal proportional to the amount of light detected. The signal is preamplified in preamplifier 280 and sent to two sample and hold circuits 282 and 284. Sample and hold circuit 282 is gated to sample the "base line", or voltage level when the light source is turned off. Refer to waveform $T_1$ in FIG. 25. Sample and hold circuit 284 is gated to sample the light detected by photodetector 234 when light source 232 is on. Refer to waveform $T_0$ in FIG. 25. The outputs of sample and hold circuits 282 and 284 are sent to difference amplifier 286. The output of difference amplifier 286 is thus substantially the difference between light levels detected by photodetector 234 when light source 232 is energized and when it is off. Since the time interval between pulses $T_1$ and $T_0$ is on the order of 40 usec, it will be seen that the clot detection electronics are thus independent of ambient lighting, since only the difference between the light emitted by light source 232 and the ambient light level is used. There will be essentially no change in ambient lighting over a 40 usec period. Moreover, a 40 usec period renders the detection electronics insensitive to 50 Hz or 60 Hz flicker, which is always present in ambient lighting.

The output of difference amplifier 286 is differentiated in differentiator circuit 288 and further amplified. By differentiating the signal, the rate of change of optical transmissivity of the plasma sample is detected. By using the rate of change instead of an absolute change in transmissivity, coagulation end point can be measured independent of initial color variations or density variations within the plasma sample. The amplified differentiated signal is sent to input multiplexer 290. The undifferentiated output of the difference amplifier 286 is also sent to input multiplexer 290. Thus, either the undifferentiated or differentiated difference signal is available to microprocessor 238. The selected output of input multiplexer 290 is converted to digital form in analog-to-digital converter 292 and is sent to the microprocessor 238, which further processes the signal and calculates coagulation end point.

F. Microprocessor Sample Selection Logic

Figure 26:
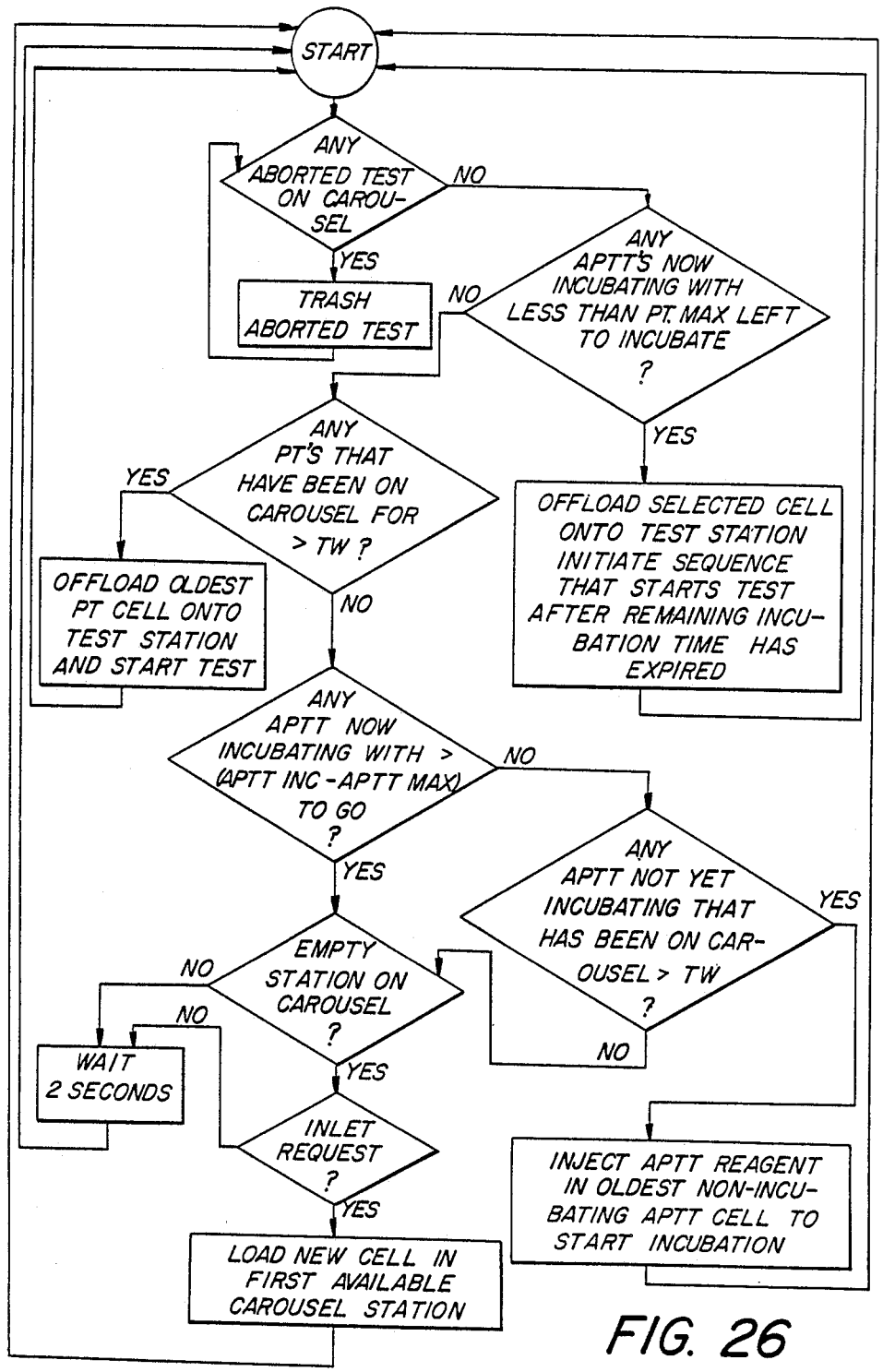
FIG. 26 is a flow chart showing decision criteria by which the next sample to be tested is selected by the microprocessor in the apparatus of the present invention.

Microprocessor sample selection logic is illustrated by the flow chart in FIG. 26. Each time a test is to be selected the microprocessor determines whether or not any test samples which may have been aborted for any reason are on the carousel. If so, the aborted test sample is ejected from the carousel. Checking for aborted test samples continues until no more aborted test samples remain on the carousel. When no more aborted test samples remain on the carousel, the microprocessor then determines whether or not any APTT tests are incubating on the carousel and are within a predetermined time of completeing their incubation period. If so, the selected cell is offloaded onto the test station and the test sequence is initiated after the remaining incubation period has expired. If not, the microprocessor determines whether or not any PT test samples are on the carousel and have been there for more than the predetermined warm-up time, $T_W$. If so, the PT test sample is offloaded onto the test station and the test is started. If not, the microprocessor then looks to determine whether or not any APTT test cells currently incubating have been incubating for less than a predetermined maximum APTT test time, $APTT_{MAX}$. If the answer is no, microprocessor determines whether any APTT test not yet incubating has been on the carousel for more than the minimum warm-up time, $T_W$. If so, APTT reagent is injected into the nonincubating APTT cell which has been on the carousel the longest to start incubation, and the microprocessor returns to the start sequence. If the answer to the previous question is yes, the microprocessor looks to see whether or not there is an empty station on the carousel. If there is an empty station on the carousel, and a test sample is ready to be loaded into the carousel, the new test cell is loaded in the first available carousel station and the start sequence is initiated. If there are no empty stations on the carousel, the microprocessor waits two seconds and then initiates the start sequence. The same is true if not test has been requested.

It will be recognized by those skilled in the art that the micropocessor decision logic described above enables the apparatus to achieve optimum sample cell throughput. Tests may be performed in the most efficient order, not necessarily the order in which sample cells are loaded onto the conveyor. Thus, tests may be carried out in any order irrespective of the order in which test samples are put into the apparatus.

G. Pneumatic System

The pneumatic system is illustrated in simplified terms in FIGS. 20A and 20B. An air compressor 294 driven by the ac power to the apparatus charges a 20 psi reservoir 296 via a check valve 300. Pressure in reservoir 296 is controlled by a pressure switch 298. Air at 20 psi is supplied to the solenoid valves 316 which control the operation of various system components (as described in connection with FIG. 22) via line 320. Solenoid valves 316 are opened or closed by microprocessor 238 as required to operate the various air cylinders. Air cylinder 132 moves the index/filtering station head 130 up and down. Cylinder 170 indexes the sample cell. Cylinder 312 moves a sample cell from the carousel to the test station and ejects samples to be discarded. Cylinder 188 operates the pre-test reagent plate 180. Cylinder 198 operates the test head 196. Cylinder 314 operates the test station stop pin 315, which limits movement of pawl 313 operated by cylinder 312 so that a test cell placed at test station is ejected only at the end of testing. The remaining elements in FIGS. 20A and 20B are numbered to correspond to the parts in individual subsystem block diagrams FIGS. 21-25.

The air supply of 20 psi is reduced to approximately 3 psi by pressure regulator 322. Pressure regulator 322 feeds solenoid controlled valves 324 and 326, which supply 3 psi air to indexing/filtering station 36. That is, solenoid valves 324 and 326 supply air to chambers 146 and 148 of indexing/filtering head 130 to move the whole blood back and forth between reservoirs 124 for filtering.

Air at 20 psi is also supplied to solenoid valve 328 which supplies air to cylinder 314.

The present invention may be embodied in other specific forms without departing from the spirit or essential attributes therof and, accordingly, reference should be made to the appended claims, rather than to the foregoing specification, as indicating the scope of the invention.

We claim:

1. Apparatus for receiving a sample of a fluid to be tested and a test reagent, comprising:

(a) slide means having at least one cavity in a top surface thereof for receiving and holding a quantity of fluid to be tested, and
    (b) body means slideably engaged with said slide means, said slide meand being slidable between a first position relative to said body means and a second position relative to said body means, a bottom surface of said body means facing the top surface of said slide means,
    (c) said body means having at least one opening therethrough from its top surface to its bottom surface, said opening being in alignment with said at least one cavity in said slide means when said slide means is in said first position whereby fluid to be tested is introduced into said cavity through said opening,
    (d) said body means also having at least one downwardly opening chamber therein, a lower end of said chamber being in the same plane as the bottom surface of said body means and being substantially open and an upper end of said chamber being substantially closed except for an opening therethrough, said chamber having a downwardly projecting member extending from said upper end of said chamber into said chamber, said chamber being in alignment with said at least one cavity in said slide means when said slide means is in said second position to form a test cell comprising said chamber and said cavity, said member being of a length such that the lowermost end thereof is below the surface of the fluid to be tested and reagent is said test cell, said member being adapted to conduct light from a light source through the fluid and the reagent in said test cell for enabling automated inspection of the fluid and the reagent in said test cell,
    (e) the top surface of said slide means being in sliding contact with the bottom surface of said body means to form means for removing excess fluid to be tested from said at least one cavity as said slide means moves relative to said body means from said first position to said second position to cause a precise, accurate volume of fluid to remain in said cavity.

2. Apparatus according to claim 1, wherein the slide means and body means are made from a material transparent to electromagnetic radiation from near-infrared to ultraviolet frequencies.

3. Apparatus according to claim 1, further comprising stop means for preventing overtravel of said slide means from said first position to said second position.

4. Apparatus according to claim 1, wherein the number of cavities in the slide means, the number of openings through said body means and the number of downwardly openings chambers in said body means is equal to two.

5. Apparatus according to claim 1, wherein said slide means includes means between said slide means and said body means for trapping air bubbles in said fluid to be tested as said fluid is introduced into said cavity.

6. Apparatus for receiving a sample of fluid to be tested and a test reagent, said fluid containing non-fluid components, and for filtering said non-fluid components from said fluid, comprising:

(a) slide means having at least one cavity in a top surface thereof for receiving and holding a quantity of filtered fluid to be tested, (b) body means slideably engaged with said slide means, said slide means being slidable between a first position relative to said body means and a second position relative to said body means, a bottom surface of said body means facing the top surface of said slide means, (c) said body means having a plurality of fluid flow channels in a top surface and at least one opening therethrough from said channels to the bottom surface of said body means, said opening communicating with said at leasst one cavity in said slide means when said slide means is in said first position to deliver filtered fluid to said cavity, (d) fluid reservoir means located on the top surface of said body means above said fluid flow channels, said fluid reservoir means having two chambers, each chamber having a top and a bottom end and being substantially open at its top end and substantially closed at is bottom end except for an opening therethrough, said opening communicating with said fluid flow channels, and (e) filter means located between said fluid flow channels and said openings in the bottom ends of said fluid reservoir chambers for filtering said non-fluid components from said fluid, (f) said body means also having at least one downwardly opening chamber therein separate from said fluid reservoir, a lower end of said chamber being in the same plane as the bottom surface of said body means and being substantially open and an upper end of said chamber being substantially closed except for an opening therethrough, said chamber having a downwardly projecting member extending from said upper end of said chamber into said chamber, said chamber being in alignment with said at least one cavity in said slide means when said slide means is in said second position to form a test cell comprising said chamber and said cavity, said member being of a length such that the lowermost end thereof is below the surface of the fluid to be tested and reagent in said test cell, (g) the top surface of said slide means being in sliding contact with the bottom surface of said body means to form means for removing excess fluid to be tested from said at least one cavity as said slide means moves relative to said body means from said first position to said second position to cause a precise accurate volume of fluid to remain in said cavity.

7. Apparatus according to claim 6, wherein the slide means, body means and reservoir means are made from a material transparent to electromagnetic radiation from near-infrared to ultraviolet frequencies.

8. Apparatus according to claim 6, further comprising stop means for preventing overtravel of said slide means from said first position to said second position.

9. Apparatus according to claim 6, wherein said filter means comprises a porous polycarbonate sheet.

10. Apparatus according to claim 6, wherein said number of cavities in the top surface of said slide means and the number of said downwardly opening chambers in said body means is equal to two.

11. Apparatus according to claim 6, wherein the fluid flow channels are arranged in parallel rows.

12. Apparatus according to claim 6, wherein said slide means includes means between said slide means and said body means for trapping air bubbles in said fluid to be tested as said fluid is delivered to said cavity.

* * * * *